(12) United States Patent
Datta et al.

(10) Patent No.: US 6,315,765 B1
(45) Date of Patent: Nov. 13, 2001

(54) ELASTICIZED ABSORBENT PAD

(75) Inventors: Paul Joseph Datta; Kathy Geralyn Richardson, both of Appleton, WI (US); Sirlei Auler Waterhouse, Cincinnati, OH (US); Bernhardt Edward Kressner, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/370,439

(22) Filed: Aug. 9, 1999

Related U.S. Application Data

(63) Continuation-in-part of application No. 08/844,291, filed on Apr. 18, 1997, now abandoned, which is a continuation-in-part of application No. 08/785,737, filed on Jan. 17, 1997, now abandoned.

(51) Int. Cl.$^7$ .............................. A61F 13/15; A61F 13/20
(52) U.S. Cl. ............... 604/385.24; 604/358; 604/385.01; 604/385.101; 604/385.27; 604/385.28
(58) Field of Search .................. 604/385.24, 385.27, 604/385.31, 385.04, 358, 385.28

(56) References Cited

U.S. PATENT DOCUMENTS

| Re. 33,106 | 11/1989 | Beckestrom . |
|---|---|---|
| 2,893,393 | 7/1959 | Pressley . |
| 4,324,245 | 4/1982 | Mesek et al. . |

(List continued on next page.)

FOREIGN PATENT DOCUMENTS

| 0 091 412 B2 | 10/1983 | (EP) . |
|---|---|---|
| 0 442 223 A1 | 8/1991 | (EP) . |
| 0 520 884 A1 | 12/1992 | (EP) . |
| 0 534 488 A1 | 3/1993 | (EP) . |
| 0 604 764 A1 | 7/1994 | (EP) . |
| 0 606 082 A1 | 7/1994 | (EP) . |
| 0 617 605 B1 | 10/1994 | (EP) . |
| 0 638 303 A1 | 2/1995 | (EP) . |
| 2 188 532 B | 10/1987 | (GB) . |
| 2 195 541 A | 4/1988 | (GB) . |
| 2 266 055 B | 10/1993 | (GB) . |
| 2 296 445 A | 7/1996 | (GB) . |
| 7-112007 A | 5/1995 | (JP) . |
| 8-117271 A | 5/1996 | (JP) . |
| WO 91/07155 A1 | 5/1991 | (WO) . |
| WO 92/07536 A1 | 5/1992 | (WO) . |
| WO 983/10733 A1 | 6/1993 | (WO) . |
| WO 93/12745 A1 | 7/1993 | (WO) . |
| WO 93/12747 A1 | 7/1993 | (WO) . |

(List continued on next page.)

OTHER PUBLICATIONS

TAPPI Official Test Method T 543 om–94, "Bending Resistance of Paper (Gurley Type Tester)," published by the TAPPI Press, Atlanta, Georgia, 1994, pp. 1–5.

*Primary Examiner*—John G. Weiss
*Assistant Examiner*—Michele Kidwell
(74) *Attorney, Agent, or Firm*—Patricia A. Charlier; Thomas J. Connelly

(57) ABSTRACT

An absorbent pad having elasticized side flaps is adapted to provide improved leakage performance and comfort. In one embodiment, the elastic member of each side flap is at least partly out of the plane of the absorbent assembly when the absorbent pad is in a generally flat position, and the absorbent pad has a Gurley stiffness of greater than 2000 milligrams. In another embodiment, the absorbent pad has an anti-roll back feature and an Effective Elastic Value of at least 30 millimeters.

118 Claims, 13 Drawing Sheets

U.S. PATENT DOCUMENTS

| | | |
|---|---|---|
| 4,579,556 | 4/1986 | McFarland . |
| 4,668,230 | 5/1987 | Damico et al. . |
| 4,695,278 | 9/1987 | Lawson . |
| 4,699,823 | 10/1987 | Kellenberger et al. . |
| 4,701,177 | 10/1987 | Ellis et al. . |
| 4,704,116 | 11/1987 | Enloe . |
| 4,770,657 * | 9/1988 | Ellis et al. ............ 604/385 |
| 4,772,282 | 9/1988 | Oakley . |
| 4,808,178 | 2/1989 | Aziz et al. . |
| 4,834,740 | 5/1989 | Suzuki et al. . |
| 4,846,823 | 7/1989 | Enloe . |
| 4,865,597 | 9/1989 | Mason, Jr. et al. . |
| 4,900,317 | 2/1990 | Buell . |
| 4,944,735 | 7/1990 | Mokry . |
| 4,950,264 | 8/1990 | Osborn, III . |
| 5,009,653 | 4/1991 | Osborn, III . |
| 5,032,120 | 7/1991 | Freeland et al. . |
| 5,032,121 | 7/1991 | Mokry . |
| 5,074,856 * | 12/1991 | Coe et al. ............ 604/385.1 |
| 5,092,860 | 3/1992 | Pigneul . |
| 5,147,343 | 9/1992 | Kellenberger . |
| 5,181,563 | 1/1993 | Amaral . |
| 5,192,606 | 3/1993 | Proxmire et al. . |
| 5,234,422 | 8/1993 | Sneller et al. . |
| 5,275,590 | 1/1994 | Huffman et al. . |
| 5,292,316 | 3/1994 | Suzuki . |
| 5,308,346 | 5/1994 | Sneller et al. . |
| 5,387,210 | 2/1995 | Murakami . |
| 5,391,162 | 2/1995 | Widlund et al. . |
| 5,403,301 | 4/1995 | Huffman et al. . |
| 5,413,570 | 5/1995 | Enloe . |
| 5,415,644 | 5/1995 | Enloe . |
| 5,486,166 | 1/1996 | Bishop et al. . |
| 5,490,846 | 2/1996 | Ellis et al. . |
| 5,509,915 | 4/1996 | Hanson et al. . |
| 5,554,142 | 9/1996 | Dreier et al. . |
| 5,599,334 | 2/1997 | Johnston et al. . |
| 5,599,338 | 2/1997 | Enloe . |
| 5,613,961 | 3/1997 | DiPalma et al. . |
| 5,618,283 | 4/1997 | Yamamoto . |
| 5,649,917 | 7/1997 | Roberts et al. . |
| 5,730,738 | 3/1998 | McFall et al. . |
| 5,810,800 * | 9/1998 | Hunter et al. ............ 604/385.2 |
| B1 3,860,003 | 6/1990 | Buell . |
| B1 4,217,901 | 6/1996 | Bradstreet et al. . |
| B1 4,490,148 | 11/1986 | Beckestrom . |
| B2 4,636,207 | 11/1989 | Buell . |

FOREIGN PATENT DOCUMENTS

| | | |
|---|---|---|
| WO 93/19711 A1 | 10/1993 | (WO) . |
| WO 93/22997 A1 | 11/1993 | (WO) . |
| WO 95/07063 A1 | 3/1995 | (WO) . |
| WO 95/08972 A1 | 4/1995 | (WO) . |
| WO 95/31952 A1 | 11/1995 | (WO) . |
| WO 96/20679 A3 | 7/1996 | (WO) . |
| WO 96/23471 | 8/1996 | (WO) . |
| WO 98/31320 A1 | 7/1998 | (WO) . |

* cited by examiner

ELASTICIZED ABSORBENT PAD

This application is a continuation-in-part of U.S. patent application Ser. No. 08/844,291 filed Apr. 18, 1997, now abandoned, which is a continuation-in-part of U.S. patent application Ser. No. 08/785,737 filed Jan. 17, 1997 now abandoned.

BACKGROUND OF THE INVENTION

The present invention relates to disposable absorbent articles. More particularly, the invention pertains to elasticized absorbent pads that are adapted to assume and maintain an effective bucket shape during use.

Absorbent pads for menstruation or urinary incontinence are intended to absorb and retain body fluids. Such pads typically comprise an absorbent structure disposed between a fluid (or liquid) permeable topsheet and a fluid (or liquid) impermeable backsheet. Leakage to the side has been a problem when using absorbent pads. This has been a problem in all types of absorbent pads, both the older types, i.e. thick and wide pads, and in more modern types, e.g. so-called body-shaped pads, which vary in thickness along their lengths and are relatively narrow in the mid-section where the pads are thickest.

The older uniformly thick pads are often greatly deformed during use quite simply because the pads are too large and not fitted to the shape of the human body. Such pads are not resilient and deform with the movement of the wearer's body. The pads usually press together in the mid-section and bend along a longitudinal axis such that the garment-facing side folds back onto itself and the body-facing surface becomes convex with portions of the topsheet layer facing out toward the sides of the pads, resulting in a reduction in effective fluid-retention. Leakage results from the folding and shifting movement of the pad.

Attempts to solve these problems have resulted in pads having shapes that follow the shape of the body and having the greatest absorption capacity where the need is greatest. These modern pads do not deform especially much during use and are typically more comfortable. However, side leakage is still a substantial problem even in the body-shaped pads. On occasions when fluid discharge is great, not all the fluid is absorbed rapidly enough, rather, a portion of the fluid can leak out to the sides of the pad.

More recent developments have resulted in thinner pads. This has been made possible both by compressing the absorbent material, and by using high-absorbent materials. However, side leakage is still a problem as such pads do not conform to the body. Since the pads are usually very thin, the pads must be relatively broad even in the middle, making the pads liable to be greatly deformed during use, unfortunately often resulting in side leakage.

Many pads leak when an insult of fluid escapes off the side edges of the pad before the fluid can be absorbed. This leakage is more likely to occur after multiple insults when the absorbent assembly or core is more saturated. Many pads have the ability to maintain contact between the pad and the wearer's body when the pad is dry. Unfortunately, after at least one insult of fluid, the body-facing surface of the absorbent assembly or core shifts, swelling upward or drawing downward to the point of disrupting contact between the pad and the wearer's body. This disruption reduces the effective gasketing along the side edges of the pad.

Many different attempts have been made to eliminate the occurrence of side leakage. In thin pads, one example is to arrange a number of longitudinal compressed areas in the absorbent assembly or core for the purpose of rapidly spreading the fluid longitudinally. These compressed areas are, however, far from sufficient to satisfactorily eliminate side leakage.

It is also known to further widen the fluid-impermeable backsheet layer so as to cover, in addition to the back and side edges of the pad, also a portion of the body-facing surface. In such a design, the fluid already collected in the absorbent assembly or core is effectively enclosed. However, there is the substantial disadvantage in that the fluid-impermeable backsheet layer is folded in over a portion of the body-facing surface, covering a major portion of the body-facing surface of the pad. When the pad is deformed during use, fluid can run directly out of the pad over the portions of the backsheet layer folded over the body-facing surface.

Absorbent pads have also incorporated elastic members in an attempt to form a bowed shaped or a bucket-shaped product with the goal of better fluid containment and improved leakage performance. Present elasticized pads have been less than successful in achieving this goal. One reason is that the elasticized sides of many existing pads create ineffective barriers to fluid movement. In some current absorbent pads, for example, the elastic structures tend mainly to bunch the pad, and particularly tend to bunch the absorbent assembly or core in the central portion of the pad. As a consequence of ineffective elastic utilization, current absorbent pads are subject, much too commonly, to failure in the form of leakage.

Thus, there is a need for an absorbent pad with elasticized side flaps that provides a bucket-shaped receptacle with effective elastic members. In addition, there is a need for an absorbent pad with effective gasketing characteristics creating a barrier that reduces side leakage not only when the pad is dry but also after multiple insults and heavier fluid loads.

SUMMARY OF THE INVENTION

It has now been discovered that the performance and even comfort of disposable absorbent pads can be enhanced by constructing the pads with more effective elasticized side flaps. The term "absorbent pads" is used herein to refer to devices to absorb and retain bodily discharges that do not rely on belts, diaper-like fastening tapes or elastic straps for proper positioning. Thus, the term "absorbent pads" includes a variety of pads, guards and sanitary napkins that may be used for urinary incontinence or menstruation. The term "disposable" includes being disposed of after use and not intended to be washed and reused.

In one embodiment, an absorbent pad defines longitudinal and transverse axes and comprises a backsheet layer, a fluid permeable topsheet layer superposed on the backsheet layer, and an absorbent assembly sandwiched between the backsheet layer and the topsheet layer. Side flaps of the absorbent pad are disposed transversely outward of the absorbent assembly, and each side flap comprises an elastic member that is at least partly out of the plane of the absorbent assembly when the absorbent pad is in a generally flat position. The absorbent pad has a Gurley stiffness of greater than 2000 milligrams.

In another embodiment, an absorbent pad defines a longitudinal axis, a transverse axis, opposite longitudinal end edges, and opposite longitudinal side edges extending between the longitudinal end edges. The absorbent pad comprises a backsheet layer, a fluid permeable topsheet layer superposed on the backsheet layer, and an absorbent assembly sandwiched between the backsheet layer and the topsheet layer. Side flaps are disposed transversely outward of the absorbent assembly. Each side flap comprises an elastic member having opposite active ends that are longitudinally spaced from the respective longitudinal end edges of the absorbent pad. Garment attachment means are disposed on the backsheet layer remote from the absorbent assembly. The garment attachment means are positioned and extend longitudinally outward of the active ends of the elastic members. The absorbent pad has an Effective Elastic Value of at least 30 millimeters.

In another embodiment, an absorbent pad defines longitudinal and transverse axes and comprises a backsheet layer, a fluid permeable topsheet layer superposed on the backsheet layer, and a single layer absorbent core sandwiched between the backsheet layer and the topsheet layer. Side flaps of the absorbent pad are disposed transversely outward of the absorbent core, and each side flap comprises an elastic member that is at least partly out of the plane of the absorbent core when the absorbent pad is in a generally flat position. The absorbent pad has a Gurley stiffness of greater than 800 milligrams.

In another embodiment, an absorbent pad defines a longitudinal axis, a transverse axis, opposite longitudinal end edges, and opposite longitudinal side edges extending between the longitudinal end edges. The absorbent pad comprises a backsheet layer, a fluid permeable topsheet layer superposed on the backsheet layer, and an absorbent core sandwiched between the backsheet layer and the topsheet layer. Side flaps are disposed transversely outward of the absorbent core. Each side flap comprises an elastic member having opposite active ends that are longitudinally spaced from the respective longitudinal end edges of the absorbent pad. Garment attachment means are disposed on the backsheet layer remote from the absorbent core. The garment attachment means are positioned and extends longitudinally outward of the active ends of the elastic members. The absorbent pad has an Effective Elastic Value of at least 30 millimeters.

In another embodiment, an absorbent pad defines longitudinal and transverse axes and comprises a backsheet layer, a fluid permeable topsheet layer superposed on the backsheet layer, and an absorbent assembly (or a single layer absorbent core) sandwiched between the backsheet layer and the topsheet layer. Side flaps of the absorbent pad are disposed transversely outward of the absorbent core, and each side flap comprises an elastic member that is at least partly out of the plane of the absorbent assembly (or absorbent core) when the absorbent pad is in a generally flat position. The side flaps are folded during use prior to an insult of fluid on the absorbent pad. The side flaps at least partially unfolded during use after at least one insult of fluid on the absorbent pad.

In another embodiment, an absorbent pad defines a longitudinal axis, a transverse axis, opposite longitudinal end edges, and opposite longitudinal side edges extending between the longitudinal end edges. The absorbent pad comprises a backsheet layer, a fluid permeable topsheet layer superposed on the backsheet layer, and an absorbent assembly (or absorbent core) sandwiched between the backsheet layer and the topsheet layer. Side flaps are disposed transversely outward of the absorbent assembly (or absorbent core). Each side flap comprises an elastic member having opposite active ends that are longitudinally spaced from the respective longitudinal end edges of the absorbent pad. The side flaps are folded during use prior to an insult of fluid on the absorbent pad. The side flaps at least partially unfolded during use after at least one insult of fluid on the absorbent pad. Garment attachment means are disposed on the backsheet layer remote from the absorbent assembly (or absorbent core). The garment attachment means are positioned and extend longitudinally outward of the active ends of the elastic members. The absorbent pad has an Effective Elastic Value of at least 30 millimeters.

In another embodiment, an absorbent pad defines longitudinal and transverse axes and comprises a backsheet layer, a fluid permeable topsheet layer superposed on the backsheet layer, an absorbent assembly sandwiched between the backsheet layer and the topsheet layer. Side flaps of the absorbent pad are disposed transversely outward of the absorbent assembly, and each side flap comprises an elastic member that is at least partly out of the plane of the absorbent assembly when the absorbent pad is in a generally flat position. Each side flap of the absorbent pad maintains an upward gasketing contact relationship with a wearer's body during use that creates a bucket-shaped product.

In another embodiment, an absorbent pad defines a longitudinal axis, a transverse axis, opposite longitudinal end edges, and opposite longitudinal side edges extending between the longitudinal end edges. The absorbent pad comprises a backsheet layer, a fluid permeable topsheet layer superposed on the backsheet layer, and an absorbent assembly sandwiched between the backsheet layer and the topsheet layer. Side flaps are disposed transversely outward of the absorbent assembly. Each side flap comprises a proximal edge, a distal edge, a body-facing surface which is configured to be in a contacting relationship with a wearer's body during use. Each side flap comprises at least one elastic member having opposite active ends that are longitudinally spaced from the respective longitudinal end edges of the absorbent pad. The proximal edge of each side flap is attached to the longitudinal side edges of the absorbent pad and the distal edge of each side flap remains unattached from the longitudinal side edges of the absorbent pad. The garment attachment means are disposed on the backsheet layer remote from the absorbent assembly. The garment attachment means are positioned and extend longitudinally outward of the active ends of the elastic members. The absorbent pad has an Effective Elastic Value of at least 30 millimeters.

In another embodiment, an absorbent pad defines longitudinal and transverse axes, and comprises a backsheet layer, a fluid permeable topsheet layer superposed on the backsheet layer, and a single layer absorbent core sandwiched between the backsheet layer and the topsheet layer. Side flaps of the absorbent pad are disposed transversely outward of the absorbent core. Each side flap comprises an elastic member that is at least partly out of the plane of the absorbent core when the absorbent pad is in a generally flat position. Each side flap of the absorbent pad maintains an upward gasketing contact relationship with a wearer's body during use creating a bucket-shaped product to capture and hold leakage.

In another embodiment, an absorbent pad defines a longitudinal axis, a transverse axis, opposite longitudinal end edges, and opposite longitudinal side edges extending between the longitudinal end edges. The absorbent pad comprises a backsheet layer, a fluid permeable topsheet layer superposed on the backsheet layer, and a single layer absorbent core sandwiched between the backsheet layer and the topsheet layer. Side flaps are disposed transversely outward of the absorbent core. Each side flap comprises a proximal edge, a distal edge, a body-facing surface which is configured to be in an upward gasketing contact relationship with a wearer's body during use that creates a bucket-shaped product to capture leakage. Each side flap comprises at least one elastic member having opposite active ends that are longitudinally spaced from the respective longitudinal end edges of the absorbent pad. The proximal edge of each side flap is attached to the longitudinal side edges of the absorbent pad and the distal edge of each side flap remains unattached from the longitudinal side edges of the absorbent pad. The garment attachment means are disposed on the backsheet layer remote from the absorbent core. The garment attachment means are positioned and extend longitudinally outward of the active ends of the elastic members. The absorbent pad has an Effective Elastic Value of at least 30 millimeters.

In another embodiment, an absorbent pad defines longitudinal and transverse axes, and comprises a backsheet layer, a liquid permeable topsheet layer superposed on the backsheet layer, and an absorbent assembly sandwiched between the backsheet layer and the topsheet layer. Side flaps are disposed at least partially transversely outward of the absorbent assembly. Each side flap comprises an elastic member that is at least partly out of the plane of the absorbent assembly when the absorbent pad is in a generally flat position. The absorbent pad has a Gibbosity Factor of less than about 18.

In another embodiment, an absorbent pad defines a longitudinal axis, a transverse axis, opposite longitudinal end edges, and opposite longitudinal side edges extending between the longitudinal end edges. The absorbent pad comprises a backsheet layer, a liquid permeable topsheet layer superposed on the backsheet layer, and an absorbent assembly sandwiched between the backsheet layer and the topsheet layer. Side flaps are disposed transversely outward of the absorbent assembly. Each side flap comprises an elastic member having opposite active ends that are longitudinally spaced from the respective longitudinal end edges of the absorbent pad. The garment attachment means are disposed on the backsheet layer remote from the absorbent assembly. The garment attachment means positioned and extend longitudinally outward of the active ends of the elastic member. The absorbent pad has a Gibbosity Factor of less than about 18.

In another embodiment, an absorbent pad defines longitudinal and transverse axes, and comprises a backsheet layer, a fluid permeable topsheet layer superposed on the backsheet layer, and a single layer absorbent core sandwiched between the backsheet layer and the topsheet layer. Side flaps are disposed at least transversely outward of the absorbent assembly. Each side flap comprises an elastic member that is at least partly out of the plane of the absorbent core when the absorbent pad is in a generally flat position. The absorbent pad has a Gibbosity Factor of less than about 18.

In another embodiment, an absorbent pad defines a longitudinal axis, a transverse axis, opposite longitudinal end edges, and opposite longitudinal side edges extending between the longitudinal end edges. The absorbent pad comprises a backsheet layer, a fluid permeable topsheet layer superposed on the backsheet layer, and a single layer absorbent core sandwiched between the backsheet layer and the topsheet layer. Side flaps are disposed transversely outward of the absorbent core. Each side flap comprises an elastic member having opposite active ends that are longitudinally spaced from the respective longitudinal end edges of the absorbent pad. The garment attachment means are disposed on the backsheet layer remote from the absorbent core. The garment attachment means are positioned and extend longitudinally outward of the active ends of the elastic members. The absorbent pad has a Gibbosity Factor of less than about 18.

In another embodiment, an absorbent pad defines longitudinal and transverse axes, and comprises a backsheet layer, a fluid permeable topsheet layer superposed on the backsheet layer, and an absorbent assembly sandwiched between the backsheet layer and the topsheet layer. Side flaps are disposed at least partially transversely outward of the absorbent assembly. Each side flap comprises an elastic member that is at least partly out of the plane of the absorbent assembly when the absorbent pad is in a generally flat position. Each side flap maintains a gasketing contact relationship with a wearer's body during use. The absorbent pad has a Gibbosity Factor of less than about 18.

In another embodiment, an absorbent pad defines a longitudinal axis, a transverse axis, opposite longitudinal end edges, and opposite longitudinal side edges extending between the longitudinal end edges. The absorbent pad comprises a backsheet layer, a fluid permeable topsheet layer superposed on the backsheet layer, and an absorbent assembly sandwiched between the backsheet layer and the topsheet layer. Side flaps are disposed transversely outward of the absorbent assembly. Each side flap comprises a proximal edge, a distal edge, and a body-facing surface which is configured to be in a contacting relationship with a wearer's body during use. Each side flap comprises at least one elastic member having opposite active ends that are longitudinally spaced from the respective longitudinal end edges of the absorbent pad. The proximal edge of each side flap is attached to the longitudinal side edges of the absorbent pad. The distal edge of each side flap remains unattached from the longitudinal side edges of the absorbent pad. The garment attachment means are disposed on the backsheet layer remote from the absorbent assembly. The garment attachment means are positioned and extend longitudinally outward of the active ends of the elastic members. The absorbent pad has a Gibbosity Factor of less than about 18.

In another embodiment, an absorbent pad defines longitudinal and transverse axes, and comprises a backsheet layer, a fluid permeable topsheet layer superposed on the backsheet layer, and a single layer absorbent core sandwiched between the backsheet layer and the topsheet layer. Side flaps are disposed transversely outward of the absorbent core. Each side flap comprises an elastic member that is at least partly out of the plane of the absorbent core when the absorbent pad is in a generally flat position. Each side flap maintains a gasketing contact relationship with a wearer's body during use. The absorbent pad has a Gibbosity Factor of less than about 18.

In another embodiment, an absorbent pad defines a longitudinal axis, a transverse axis, opposite longitudinal end edges, and opposite longitudinal side edges extending between the longitudinal end edges. The absorbent pad comprises a backsheet layer, a fluid permeable topsheet layer superposed on the backsheet layer, and a single layer absorbent core sandwiched between the backsheet layer and the topsheet layer. Side flaps are disposed transversely outward of the absorbent core. Each side flap comprises an proximal edge, a distal edge, and a body-facing surface which is configured to be in a gasketing contact relationship with a wearer's body during use. Each side flap comprises at least one elastic member having opposite active ends that are longitudinally spaced from the respective longitudinal end edges of the absorbent pad. The proximal edge of each side flap is attached to the longitudinal side edges of the absorbent pad. The distal edge of each side flap remains unattached from the longitudinal side edges of the absorbent pad. The garment attachment means are disposed on the backsheet layer remote from the absorbent core. The garment attachment means are positioned and extend longitudinally outward of the active ends of the elastic members. The absorbent pad has a Gibbosity Factor of less than about 18.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DETAILED DESCRIPTION OF THE PREFERRED EMBODIMENTS

With reference to FIGS. 1–5, an absorbent article formed according to the invention is shown for purposes of illustration as a disposable absorbent pad 20 for adult incontinence. Alternatively, the invention may be embodied in absorbent pads adapted specifically for absorption of menses, blood, or other body excrement.

Figure 1:
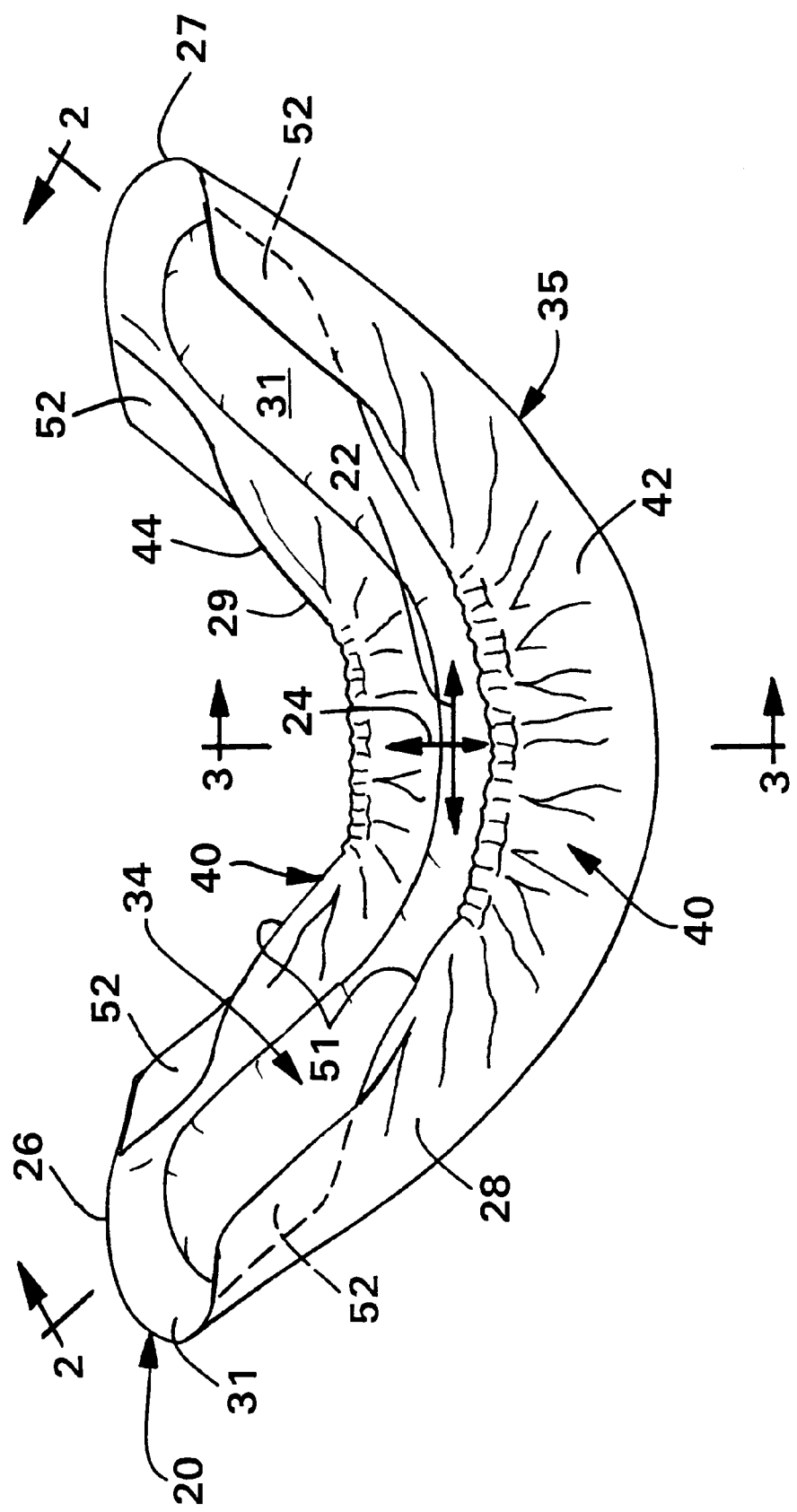
FIG. 1 representatively shows a perspective view of an absorbent pad according to the present invention.
Figure 4:
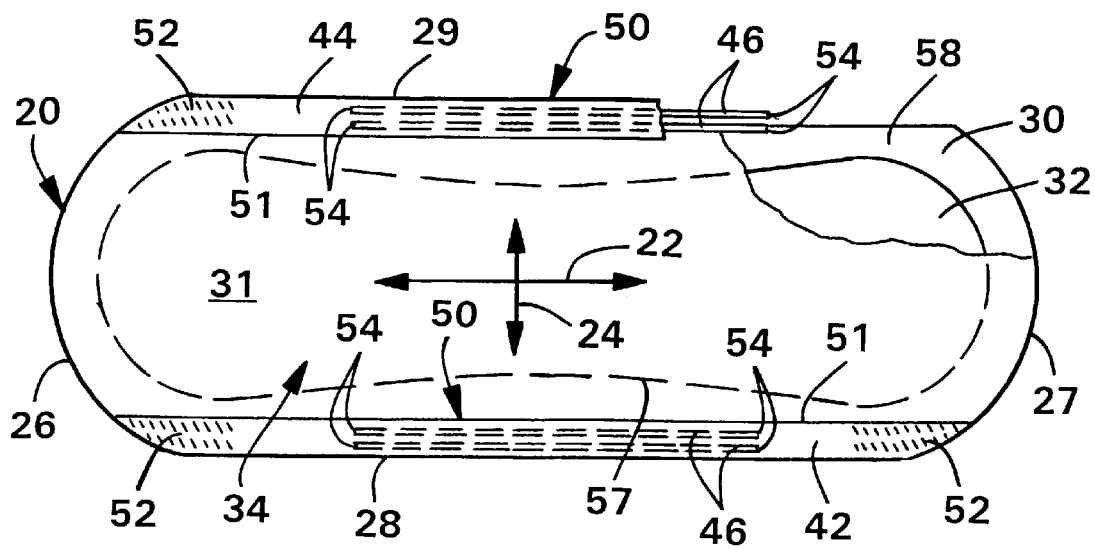
FIG. 4 representatively shows a top plan view of the absorbent pad of FIG. 1, taken from the body-facing side of the pad and in a stretched and laid flat condition, with portions broken away for purposes of illustration.

The illustrated absorbent pad 20 defines a longitudinal axis or centerline represented by arrow 22, which generally corresponds to the greatest planar dimension of the pad (FIGS. 1 and 4). A perpendicular transverse axis or centerline is represented by arrow 24. The absorbent pad 20 has opposite longitudinal end edges 26 and 27, and longitudinal side edges 28 and 29 that extend between the longitudinal end edges. The end edges 26 and 27 and side edges 28 and 29 may be straight, curvilinear or irregularly shaped. Suitable absorbent pads have a length dimension measured between the longitudinal end edges 26 and 27 of from about 10 to about 40 centimeters (cm.), more particularly from about 20 to about 30 cm., and a width dimension measured between the longitudinal side edges 28 and 29 of from about 3 to about 12 cm., more particularly from about 5 to about 10 cm.

The absorbent pad 20 includes a substantially fluid impermeable backsheet layer 30 (FIGS. 2–5 and 7–9), a fluid (or liquid) permeable topsheet layer 31 (FIGS. 1–4 and 7–9) superposed on the backsheet layer 30, and an absorbent assembly 32 (FIGS. 2–4 and 7–9) sandwiched between the backsheet layer 30 and the topsheet layer 31. The backsheet and topsheet layers 30 and 31 are desirably longer and wider than the absorbent assembly 32 (or absorbent core 33). The topsheet layer 31 is designed to be positioned toward the wearer and is referred to as the body-facing surface 34. Conversely, the backsheet layer 30 is designed to be positioned toward the undergarment of the wearer and is referred to as the garment-facing surface 35.

The backsheet layer 30 desirably comprises a material that is formed or treated to be fluid impermeable. Alternatively, the backsheet layer 30 may comprise a fluid permeable material and other suitable means (not shown), such as a fluid impermeable layer associated with the absorbent assembly 32 (or absorbent core 33), may be provided to impede fluid movement away from the absorbent assembly 32 (or absorbent core 33). The backsheet layer 30 may comprise a single layer of material or a laminate of two or more separate layers of material. Suitable backsheet layer materials include films, wovens, nonwovens, laminates of films, wovens, and/or nonwovens, rubber sheets, or the like. For example, the backsheet layer 30 may comprise a thin, substantially fluid impermeable web or sheet of plastic film such as polyethylene, polypropylene, or similar material. One suitable material for the backsheet layer 30 is a 0.028 millimeter (mm) thick polyethylene film with a systematic matte embossed pattern and that has been corona treated on both sides. The terms "fluid impermeable" or "liquid impermeable" as used herein to describe a layer or laminate means that fluid or liquid such as urine will not pass through the layer or laminate under ordinary use conditions in a direction generally perpendicular to the plane of the layer or laminate at the point of fluid (or liquid) contact.

The absorbent assembly 32 comprises materials adapted to absorb and retain urine, menses, blood, or other body excrement. The absorbent assembly 32 may comprise various natural or synthetic absorbent materials, such as cellulose fibers, surfactant treated meltblown fibers, wood pulp fibers, regenerated cellulose or cotton fibers, a blend of pulp and other fiber, or the like. One such material is a coform material which is composed of a mixture of cellulosic fibers and synthetic polymer fibers. The absorbent assembly 32 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. No. 4,699,823 issued Oct. 13, 198, to Kellenberger et al. and U.S. Pat. No. 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc. The absorbent assembly 32 may also include tissue layers or acquisition or distribution layers to help maintain the integrity of fibrous absorbents or transport fluids.

Figure 6:
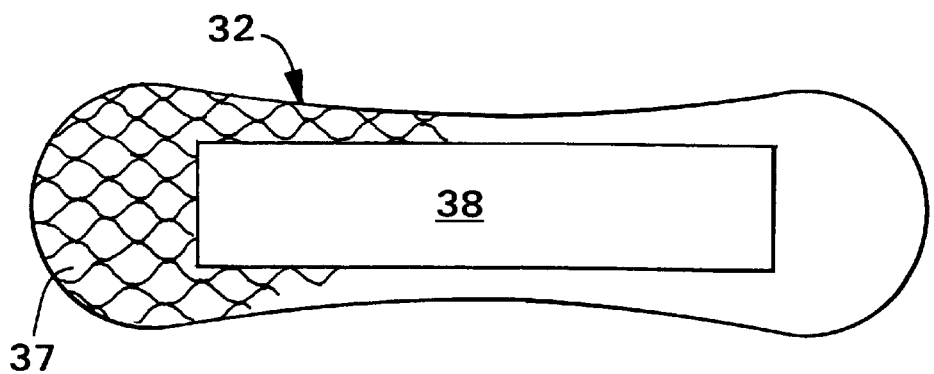
FIG. 6 representatively shows one embodiment of an absorbent assembly for use in the absorbent pad of FIG. 1.
Figure 10:
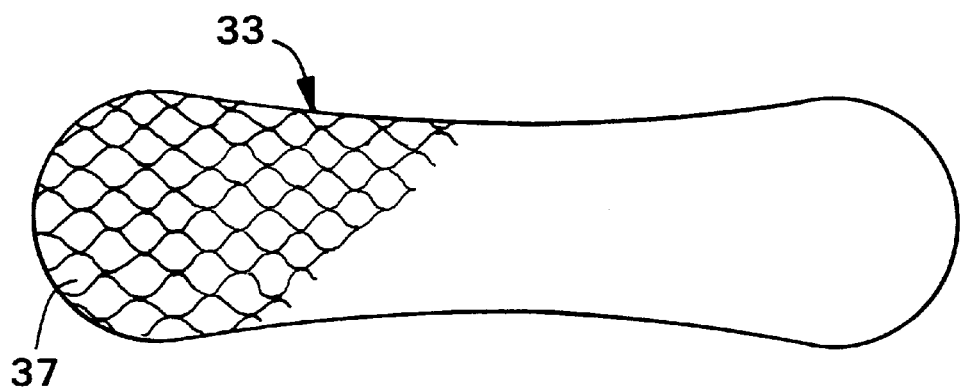
FIG. 10 representatively shows one embodiment of an absorbent core for use in the absorbent pad of FIG. 1.

One suitable absorbent assembly 32 for the absorbent pad 20 is separately illustrated in FIGS. 6 and 10 and comprises a fluid storage layer 37 and an acquisition/distribution layer 38. The storage layer 37 comprises an air-laid mixture of 470 gsm wood pulp fibers and 305 gsm high-absorbency materials that is sandwiched between a pair of 19 gsm cellulose tissues. The storage layer 37 is desirably embossed using a matched male/male embossing roll. The illustrated absorbent assembly 32 is hourglass shaped with a length of about 29.5 cm. and a width of between about 6.4 and 8.3 cm. The absorbent assembly 32 desirably has a thickness dimension of less than about 20 mm., particularly less than about 10 mm.

The acquisition/distribution layer 38 is disposed on the fluid storage layer 37 toward the body-facing surface 34 of the absorbent pad 20 to help decelerate and diffuse surges of fluid that may be introduced into the absorbent assembly 32. The acquisition/distribution layer 38 comprises a through-air bonded carded web composed of a blend of 40 percent 6 denier polyester fibers, commercially available from Hoechst Celanese Corporation, and 60 percent 3 denier polypropylene/polyethylene side-by-side bicomponent fibers, commercially available from BASF Corporation, with an overall basis weight of about 120 gsm. Alternative acquisition/distribution materials are described in U.S. Pat. No. 5,192,606 issued Mar. 9, 1993, to D. Proxmire et al.; U.S. Pat. No. 5,486,166 issued Jan. 23, 1996, to Ellis et al.; U.S. Pat. No. 5,490,846 issued Feb. 13, 1996, to Ellis et al.; and U.S. Pat. No. 5,509,915 issued Apr. 23, 1996, to Hanson et al.; the disclosures of which are hereby incorporated by reference. The illustrated acquisition/distribution layer 38 is rectangular with a length of about 19.1 cm. and a width of about 4.5 cm.

In other embodiments of the present invention, the absorbent pad 20 includes a single layer absorbent core 33 in place of the absorbent assembly 32. (See FIG. 10.) The absorbent core 33 comprises materials adapted to absorb and retain urine, menses, blood, or other body excrement. The absorbent core 33 may comprise various natural or synthetic absorbent materials, such as cellulose fibers, surfactant treated meltblown fibers, wood pulp fibers, regenerated cellulose or cotton fibers, a blend of pulp and other fiber, or the like. One such material is coform material which is composed of a mixture of cellulosic fibers and synthetic polymer fibers. The absorbent core 33 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. No. 4,699,823 issued Oct. 13, 1987, to Kellenberger et al. And U.S. Pat. No. 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc.

One suitable absorbent core 33 for the absorbent pad 20 is separately illustrated in FIGS. 7–10 and comprises a fluid storage layer 37. The storage layer 37 comprises an air-laid mixture of 470 gsm wood pulp fibers and 305 gsm high-absorbency materials that is sandwiched between a pair of 19 gsm cellulose tissues. The storage layer 37 is desirably embossed using a matched male/male embossing roll. The illustrated absorbent core 33 is hourglass shaped with a length of about 29.5 cm and a width of between about 6.4 and 8.3 cm. The absorbent core 33 desirably has a thickness dimension of less than about 20 mm, particularly less than about 10 mm.

The topsheet layer 31 is formed of a fluid permeable material so that fluid waste, and possibly semi-solid waste as well, can pass through the liner and be absorbed by the absorbent assembly 32 (or absorbent core 33). Suitable topsheet layers 31 may comprise a nonwoven web, a spunbond, meltblown or bonded-carded web composed of synthetic polymer filaments or fibers, such as polypropylene, polyethylene, polyesters or the like, a perforated film, or a web of natural polymer filaments or fibers such as rayon or cotton. In addition, the topsheet layer 31 may be treated with a surfactant to aid in fluid transfer. In one particular embodiment, the topsheet layer 31 comprises a nonwoven, spunbond web of side-by-side bicomponent filaments with 50 percent polyethylene and 50 percent polypropylene having a basis weight of about 20 grams per square meter (gsm). The fabric is surface treated with a surfactant commercially available from Union Carbide Chemicals and Plastics Company, Inc., of Danbury, Conn., U.S.A. under the trade designation TRITON X-102. As used herein, the term "fabric" refers to all of the woven, knitted and nonwoven fibrous webs. The term "nonwoven web" means a web of material that is formed without the aid of a textile weaving or knitting process.

The absorbent pad 20 includes a pair of side flaps 40 disposed along and forming the side edges 28 and 29 of the pad. The side flaps 40 are disposed transversely outward of the absorbent assembly 32 (or absorbent core 33) and may be formed partially or completely by portions of the backsheet layer 30 and/or the topsheet layer 31. In the illustrated embodiment, the side flaps 40 are formed by lateral portions of both the backsheet layer 30 and the topsheet layer 31, and by portions of two side panel members 42 and 44. The side flaps 40 include elastic members 46 (FIGS. 3–5 and 8–9) adapted to gather portions of the longitudinal side edges 28 and 29.

For purposes of the present invention, the term "side flap" refers to portions of the absorbent pad disposed transversely outward of the absorbent assembly 32 (or absorbent core 33) and at least partially gathered together by elastic structures to form impediments to lateral fluid movement. The side flaps 40 may comprise fluid permeable or fluid impermeable materials. The terms "disposed," "disposed on," "disposed with," "disposed at," "disposed near" and variations thereof are intended to mean that one element can be integral with another element, or that one element can be a separate structure bonded to or placed with or placed near another element. The terms "inward" and "outward" refer to positions relative to the center of an absorbent garment, and particularly transversely and/or longitudinally closer to or away from the longitudinal and transverse centerlines 22 and 24 of the absorbent pad 20.

In one embodiment, with particular reference to FIGS. 3–5 and 8–9, the separate side panel members 42 and 44 are desirably bonded to the backsheet layer 30 transversely outward from the longitudinal centerline 22. Each side panel member 42 and 44 includes a proximal edge 48 and an opposite distal edge 49 (FIGS. 3–5 and 8–9). In the illustrated embodiment, the proximal edges 48 are disposed on the garment-facing surface 35 of the absorbent pad 20, and the distal edges 49 are disposed in the side flaps 40. Adjacent the distal edges 49, the side panel members 42 and 44 desirably include a folded region 50 to encase the elastic members 46. The folded region 50 is thus raised above the plane of the absorbent assembly 32 (or absorbent core 33) and defines a free edge 51 of each side flap 40.

The side panel members 42 and 44 are desirably formed of a soft, gatherable material such as a spunbond nonwoven or the like. In one particular embodiment, the side panel members 42 and 44 comprise a high loft fuzzy nonwoven spunbond made of side-by-side bicomponent filaments of 50 percent polyethylene and 50 percent polypropylene.

Figure 2:
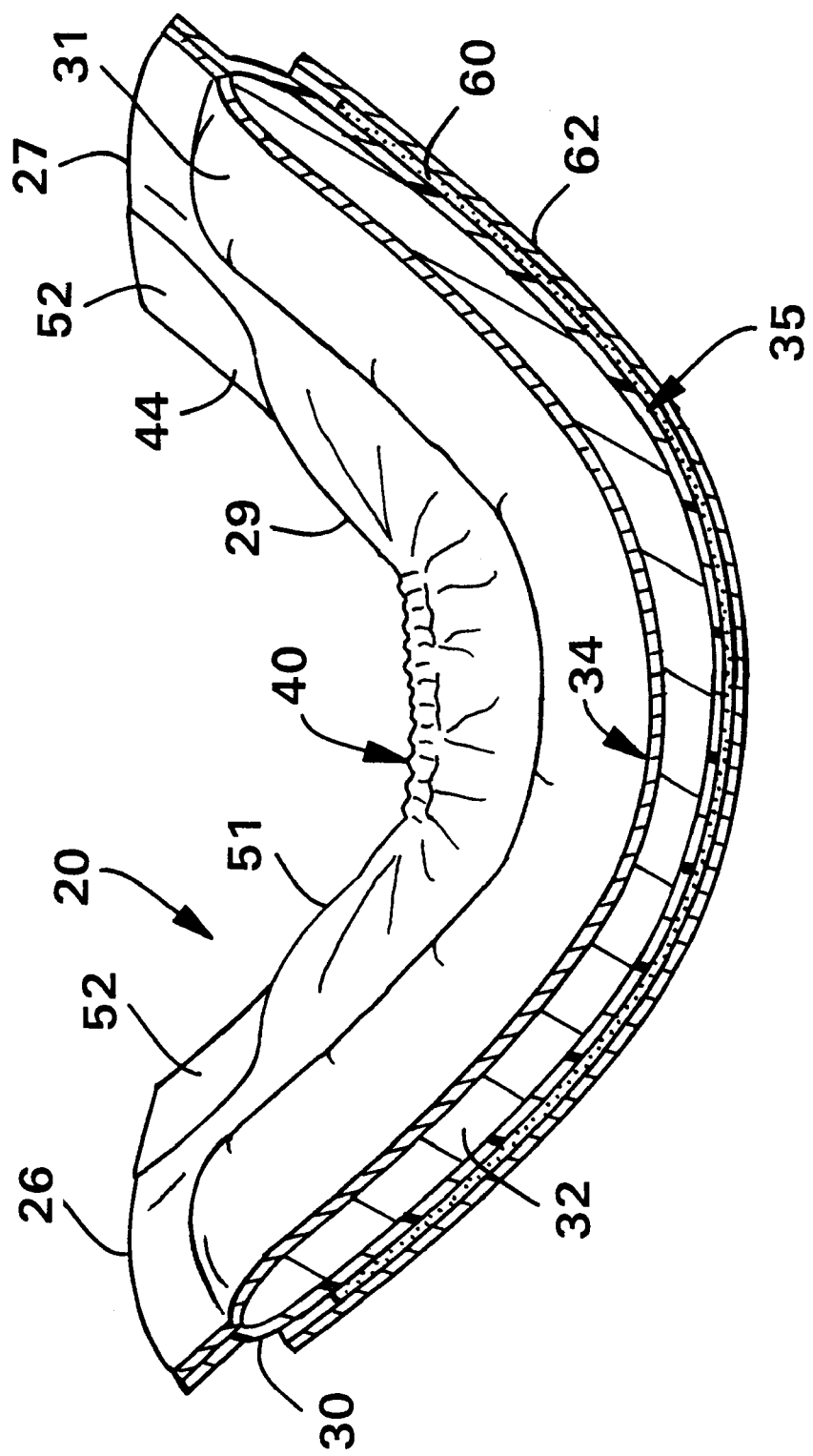
FIG. 2 representatively shows a longitudinal section view taken along line 2—2 of FIG. 1.
Figure 5:
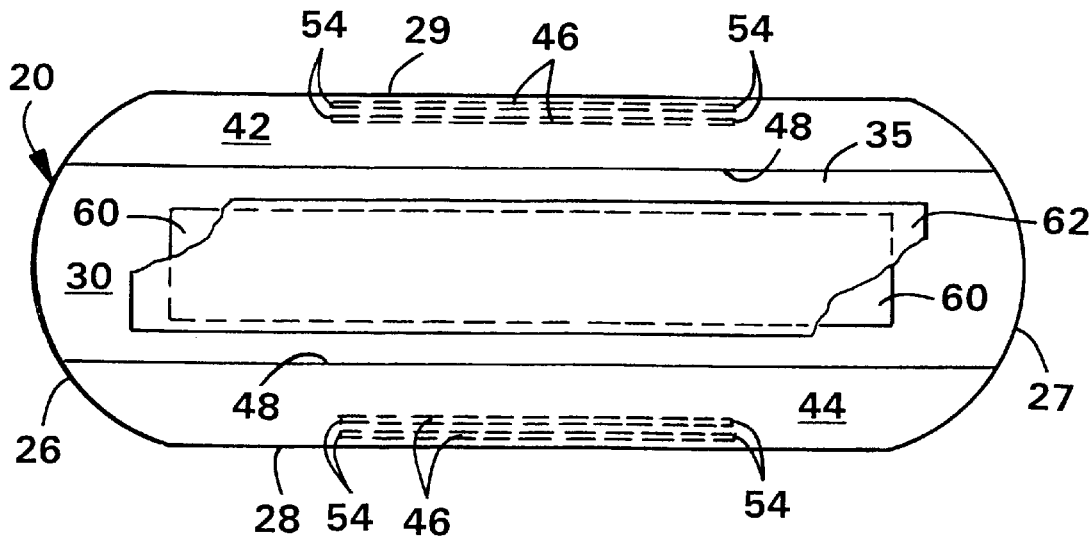
FIG. 5 representatively shows a bottom plan view of the absorbent pad of FIG. 1 taken from the garment-facing side of the pad and in a stretched and laid flat condition, with portions broken away for purposes of illustration.
Figure 7:
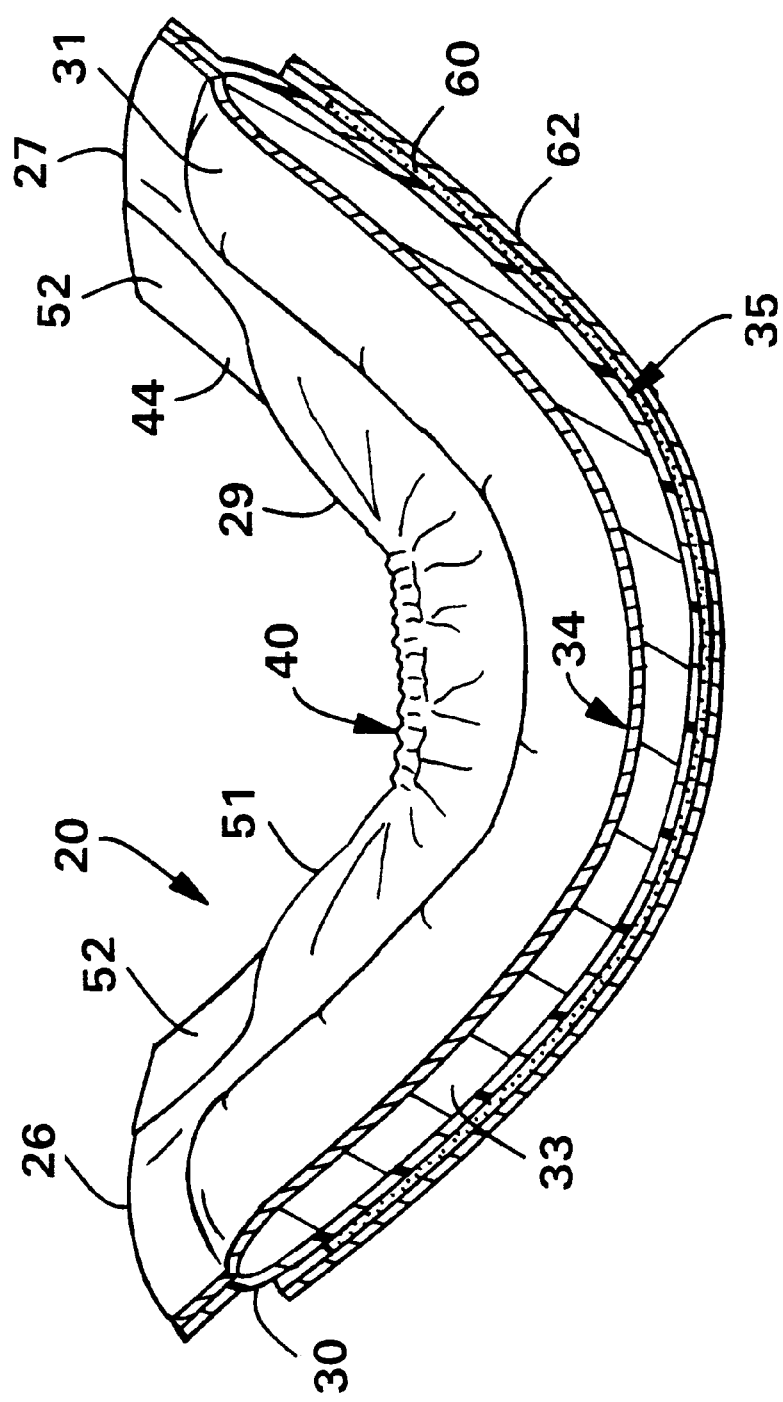
FIG. 7 representatively shows a longitudinal section view taken along line 2—2 of FIG. 1.
Figure 9:
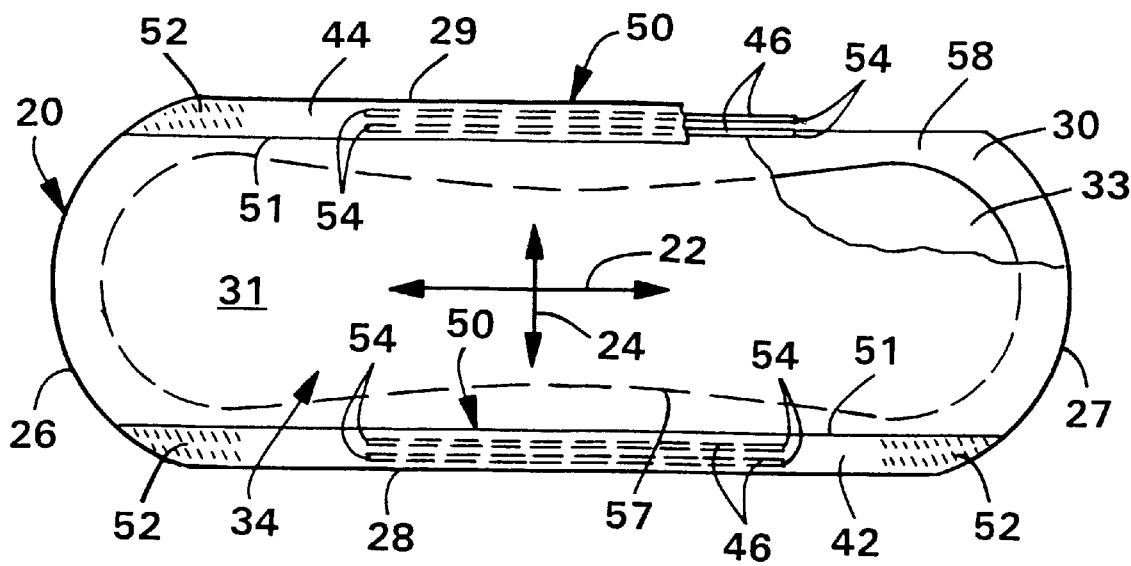
FIG. 9 representatively shows a top plan view of the absorbent pad of FIG. 1, taken from the body-facing side of the pad and in a stretched and laid flat condition, with portions broken away for purposes of illustration.

As best illustrated in FIGS. 4–5 and 9, the side flaps 40 extend the full length of the absorbent pad 20. The side flap 40 structure may be folded and bonded to itself near the longitudinal end edges 26 and 27 in order to reduce the quantity of free material in the corners. The regions 52 of the side flaps 40 that are bonded to themselves are illustrated with cross hatched lines in FIGS. 4 and 9, and the resulting inversion of the side flaps is shown in FIGS. 1–2 and 7. Alternatively, the longitudinal ends of the side flaps 40 may be folded over and bonded onto the body-facing side of the absorbent assembly 32 (or absorbent core 33), or may not be folded and bonded in place at all (not shown).

The width of the fluid impermeable backsheet layer 30 may be selected so that the backsheet layer 30 is present in at least a portion of the side flaps 40. In this case, at least a portion of the height of the side flaps 40 will be fluid impermeable. The backsheet layer 30 may be less comfortable against the skin of the wearer, and thus may be completely covered by either the topsheet layer 31 or the side panel members 42 and 44. Alternatively, the side flaps 40 may be formed completely of one or both of the topsheet layer 31 or the side panel members 42 and 44 (not shown).

The elastic members 46 are desirably operable over less than the full length of the absorbent pad 20. Each elastic member 46 has opposite active ends 54 (FIGS. 4–5 and 9) that are longitudinally spaced from the longitudinal end edges of the absorbent pad 20. As used herein, the term "active ends" refers to the terminal points of the elastic members 46 that are attached to other materials of the side flap 40 and between which the elastic member 46 is effective to gather together the side flap 40.

The elastic members 46 are longitudinally orientated in each side flap 40 and operatively joined to the side flap 40. The elastic members 46 may be bonded to the side flap 40 in a stretched condition, bonded in a relaxed state to a gathered portion of the side flap 40, or may have elastic properties activated after being bonded to the side flap 40. "Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

The elastic members 46 may be formed of a dry-spun coalesced multifilament elastomeric thread sold under the tradename LYCRA and available from E.l. Du Pont de Nemours and Company. Alternately, the elastic members 46 may be formed of other typical elastics utilized in making incontinence products, such as a thin ribbon of natural rubber, wet-spun spandex materials, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive on the side flaps 40.

The terms "elastic," "elasticized" and "elasticity" mean that property of a material by virtue of which it tends to recover its original size and shape after removal of a force causing a deformation. "Elastomeric" refers to a material or composite which can be elongated by at least 25 percent of its relaxed length and which will recover, upon release of the applied force, at least 10 percent of its elongation. It is generally preferred that the elastomeric strands be capable of being elongated by at least 100 percent of its relaxed length and recover, upon release of an applied force, at least 50 percent of its elongation.

Figure 17:
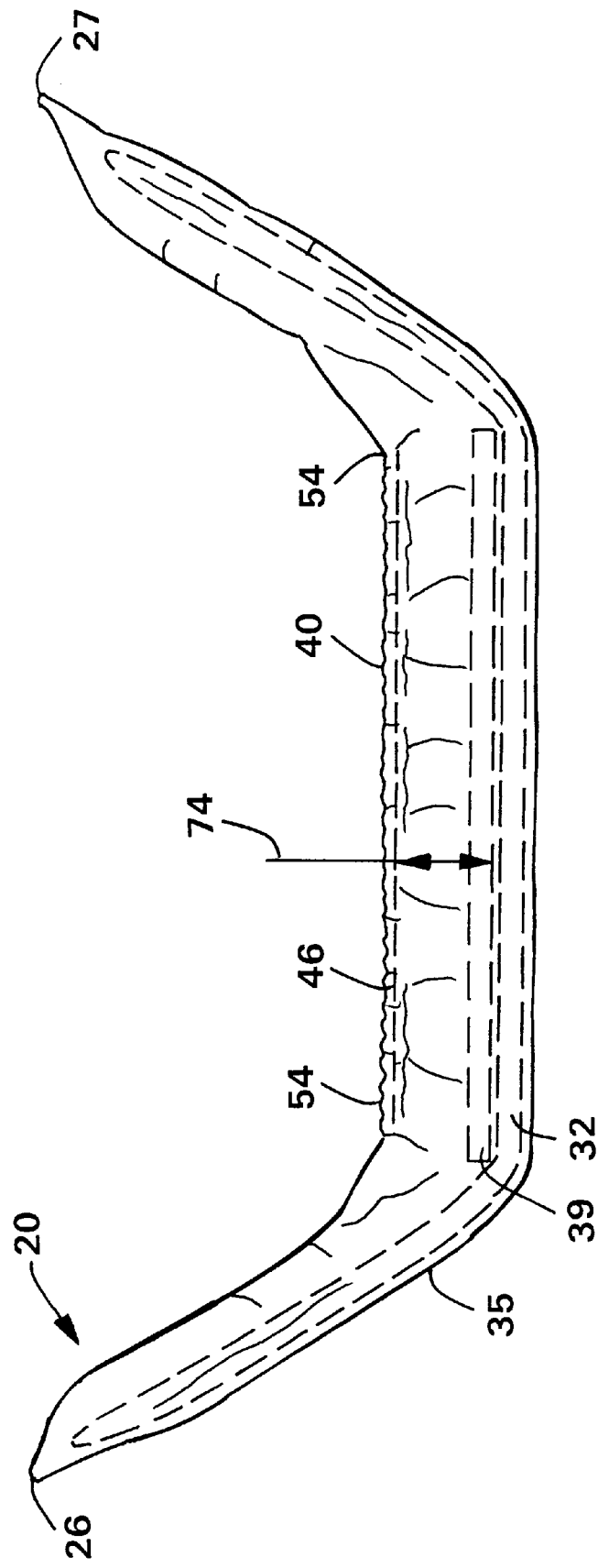
FIG. 17 representatively shows a side-view of the absorbent pad of FIG. 1.

To improve performance of the side flaps 40 in particular and the absorbent pad 20 overall, the elastic members 46 of each side flap 40 are desirably positioned at least partly out of the plane of the absorbent assembly 32 (or, in other embodiments, the absorbent core 33) when the absorbent pad 20 is in a generally flat position (see FIG. 17), as the pad 20 would be when worn by an adult. In general, an elastic member 46 is considered to be at least partly out of the plane of the absorbent assembly 32 (or absorbent core 33) when, at some point at or between the active ends 54, a portion of the elastic member 46 is disposed above the top surface of the absorbent assembly 32 (or absorbent core 33). The position of the elastic member 46 relative to the plane of the absorbent assembly 32 (or absorbent core 33) is measured while a bar 39 is resting on the center of the absorbent pad 20 to generally simulate one possible use position. If more than one elastic member 46 is disposed in a side flap 40, the elastic member 46 closest to the longitudinal centerline 22 is used to determine the position relative to the plane of the absorbent assembly 32 (or absorbent core 33).

In particularly desirable embodiments, the elastic members 46 of each side flap 40 are positioned completely out of the plane of the absorbent assembly 32 (or absorbent core 33) when the absorbent pad 20 is in a generally flat position. An elastic member 46 is considered completely out of the plane of the absorbent assembly 32 (or absorbent core 33) when both active ends 54 and all portions therebetween are disposed above the top surface of the absorbent assembly 32 (or absorbent core 33). The position of the elastic member 46 relative to the plane of the absorbent assembly 32 (or absorbent core 33) is measured while a bar 39 is resting on the center of the absorbent pad 20 to generally simulate one possible use position. (See FIG. 17.)

The configuration of the side flaps 40 is such that the elastic members 46 rise at least partially out of the plane of the absorbent assembly 32 (or absorbent core 33), allowing the side flaps 40 and the elastic members 46 to fit against or closer to the body of the wearer between the labia and the legs thereby providing a gasketing contact between the side flaps 40 and the wearer's body. The gasketing contact is provided toward the abdomen and the buttocks along nearly the entire length of the pad 20.

In addition, the configuration of the side flaps 40 of the present invention provides a bucket shaped structure. The side flaps 40 serve to stop or impede fluid migration away from the absorbent assembly 32 (or absorbent core 33) during fluid insults before the fluid has been absorbed into the absorbent assembly 32 (or absorbent core 33). Typically during fluid insults, especially insults having larger volumes, several seconds elapse before the entire insult is absorbed. During this time, the fluid flows or migrates to the edges of the absorbent article. The side flaps 40 function as a dam or barrier, retaining the fluid in proximity of the absorbent assembly 32 (or absorbent core 33) until the fluid can be absorbed. Because the elastic members 46 and the side flaps 40 extend above the plane of the absorbent assembly 32 (or absorbent core 33), a bucket shaped structure is formed in which the fluid can be retained until it is absorbed by the pad 20.

Absorbent articles lacking side flaps 40 do not provide the bucket shaped structure to retain the fluid until absorbed into the absorbent article. Absorbent articles without upward standing side flaps 40 not only hold the absorbent structure of the article closer to the body of the wearer, leaving little or no space for the fluid to be retained until absorbed, but also lack any structure to prevent or impede fluid migration away from the absorbent structure. Elastic material located at the sides of the absorbent assembly 32 (or absorbent core 33), rather than in flap structures such as side flaps 40, do not hold the fluid in the proximity of the absorbent structure long enough to allow absorption of the fluid. Rather, such elastic material assists in positioning and maintaining placement of the article and providing article sides that more comfortably accommodate the insides of the wearer's legs.

The elastic members 46 desirably have an Elastic Out Of The Plane Value, which represents the height of an elastic member 46 above the plane of the absorbent assembly 32 (or absorbent core 33), of at least about 1 mm, particularly at least about 5 mm, and more particularly of from about 10 mm to about 30 mm, and most particularly of from about 10 mm to about 100 mm for improved performance. Constructing the absorbent pad 20 to have elastic members 46 a particular height above the absorbent assembly 32 (or absorbent core 33) may require adjusting the spacing of the elastic members 46 from the absorbent assembly 32 (or absorbent core 33) and varying the degree to which the side flaps 40 are free to move independently of the absorbent assembly 32 (or absorbent core 33). In one embodiment, the elastic members 46 comprise strands of 720 denier elastomeric thread stretched 160 percent of its original length and operatively joined to the side panel members 42 and 44 with a hot melt adhesive over a distance of 16.5 cm.

One procedure for measuring the Elastic Out Of The Plane Value is an Elastic Height Test, which measures the distance of the innermost elastic member 46 to the surface of the absorbent assembly 32 (or absorbent core 33). (See FIG. 17.) Because the test is performed with the pad 20 resting on a table with the garment-facing surface 35 toward the table, the innermost elastic member 46 can be considered the "lowest" member 46. The lowest elastic member 46 is the member 46 that is closest to the garment attachment adhesive 60 side of the pad 20. The body-facing surface 34 of the absorbent pad 20 is considered the plane or surface of the absorbent assembly 32 (or absorbent core 33).

The pad 20 is placed on the top surface of a level bench with the garment-facing surface 35 toward the bench. The test employs a generally flat bar 39 of stainless steel weighing approximately 358 grams and measuring 5.7 cm wide by 12.7 cm long by 6.4 millimeters (mm) thick (2.25 by 5 by 0.25 in.). One of the major surfaces of the bar 39 is placed on the body-facing surface 34 of the pad 20, longitudinally and transversely centered relative to the absorbent assembly 32 (or absorbent core 33).

For purposes of the present invention, the absorbent pad 20 is considered to be "in a generally flat position" when the bar 39 is situated as described. The bar 39 should neither cover nor contact the side flaps 40 or the elastic members 46. Appropriate adjustments in the length of the bar 39 may be required so that the bar 39 is within about 30 to about 75 percent of the pad length, more preferably within about 30 to about 50 percent of the pad length. If the absorbent pad 20 has been bi-folded or tri-folded in the packaging process, the length of the bar 39 is adjusted such that the bar 39 extends beyond the folds of the absorbent pad 20.

Identify a portion of the elastic member 46 that is closest to the surface of the bench which corresponds to the lowest portion of the elastic member 46. The lowest portion may occur between the active ends 54 or at one of the active ends 54.

Measure the distance between the surface of the bar 39 disposed toward the pad 20 and the elastic member 46 that is closest to the bench surface at the point where elastic member 46 is closest to the bench surface. This distance is represented by the number 74 on FIG. 17. If the elastic member 46 is closer to the bench than is the surface of the bar 39, record the Elastic Out Of The Plane Value measurement as a negative value. If the elastic member 46 is further from the bench than is the surface of the bar 39, record the Elastic Out Of The Plane Value measurement as a positive value. In contrast to the Elastic Out Of The Plane Value, if the elastic member 46 is above the surface of the bar 39, that is the plane of the absorbent assembly 32 (or absorbent core 33), at any point at or between the active ends 54, the elastic member 46 is considered to be at least partly out of the plane of the absorbent assembly 32 (or absorbent core 33).

It may be difficult to see where the elastic members 46 are while measuring. If this occurs, use a very fine line magic marker, for example a SANFORD® Ultra Fine Point SHARPIE® to highlight the elastic member 46 closest to the bench surface.

Calculate the average and standard deviation for 15 sample pads 20, with one measurement per side. The average represents the Elastic Out Of The Plane Value.

Another feature impacting performance of the absorbent pad 20 is the degree of flexibility or stiffness of the absorbent portion of the pad 20. Despite a general perception that pads need to be flexible to conform to the body and remain comfortable, it has been discovered that absorbent pads 20 with a greater degree of stiffness tend to curve rather than bunch when combined with effective elastic members 46, such as elastic members 46 located out of the plane of the absorbent assembly 32 (or absorbent core 33).

In particular embodiments, for example, wherein the absorbent pad 20 includes an absorbent assembly 32, the absorbent pad 20 desirably has an average Gurley stiffness value of greater than 2000 milligrams (mg), such as from 2000 to about 15000 mg., particularly greater than about 3000 mg., such as from about 3000 to about 5000 mg., and more particularly from about 3000 to about 4500 mg., for improved performance. In one embodiment, the requisite Gurley stiffness is obtained by embossing the absorbent assembly 32 of the pad 20 with a pattern that creates soft pillows between embossing lines. Heat, moisture and pressure are used to create an embossed area that resists bunching, and soft pillows are formed between the embossments to allow the pad 20 to remain comfortable to the wearer. The desired levels of stiffness function with the elastic members 46 to enable the elastic members 46 to curve the absorbent pad 20 into the bucket shape after being unfolded and to achieve the desired smoothness of the body-facing surface 34. The desired levels of stiffness also tend to resist bunching and the formation of creases in the absorbent assembly 32 during manufacture, packaging and storage.

In other embodiments, for example, wherein the absorbent pad 20 includes an absorbent core 33, the absorbent pad 20 desirably has an average Gurley stiffness value of greater than 800 milligrams (mg), such as from 800 to about 15000 mg., particularly greater than about 1000 mg., such as from about 1000 to about 8000 mg., and more particularly from about 2000 to about 4000 mg., for improved performance. In one embodiment, the requisite Gurley stiffness is obtained by embossing the absorbent core 33 of the pad 20 with a pattern that creates soft pillows between embossing lines. Heat, moisture and pressure are used to create an embossed area that resists bunching, and soft pillows are formed between the embossments to allow the pad 20 to remain comfortable to the wearer. The desired levels of stiffness function with the elastic members 46 to enable the elastic members 46 to curve the absorbent pad 20 into the bucket shape after being unfolded and to achieve the desired smoothness of the body-facing surface 34. The desired levels of stiffness also tend to resist bunching and the formation of creases in the absorbent core 33 during manufacture, packaging and storage.

Gurley stiffness is measured according to TAPPI test procedure T543 pertaining to stiffness of paper. The clamp of the Gurley stiffness tester is modified to insert the thickness of a pad without crushing. The test is conducted using a test specimen taken from part of the absorbent pad 20 including the absorbent assembly 32 (or absorbent core 33), rather than including portions of the side and end margins of the pad 20. Also, the test specimen desirably does not include the portions of the absorbent assembly 32 (or absorbent core 33) that were folded during manufacture and packaging.

The performance of the absorbent pad 20 is improved when the side flaps 40 are effective to curve, forming a bucket, rather than simply wrinkling or bunching the pad 20. The effectiveness of the elastic members 46 is particularly important after the absorbent pads 20 have been maintained in a folded position for an extended period of time. Commercial elasticized absorbent pads are packaged in a folded condition for sale to the consumer. Maintaining the absorbent pads 20 in a folded condition for extended periods can detract from the effectiveness of the elastic members 46. In particular, if the elastic members 46 are not allowed to contract during storage, the retraction properties of the elastic members 46 may be greatly diminished. Additionally, if the absorbent pads 20 are constructed such that the elastic members 46 are disposed in the plane of the absorbent assembly 32 (or absorbent core 33), the elastic members 46 will tend to bunch the absorbent pad 20 together during storage and the elastic members 46 will not be effective when the pad 20 is unfolded.

Figure 13:
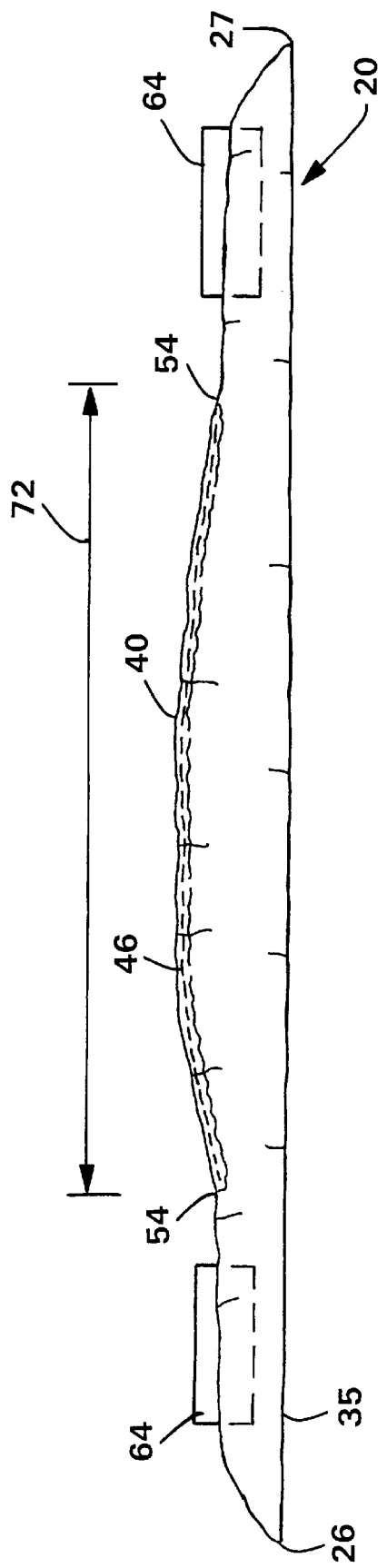
FIG. 13 representatively shows a longitudinal side view of the absorbent pad of FIG. 1, taken along line 2—2 showing the pad and the side flaps in an extended configuration.

In particular embodiments, for example, the absorbent pad 20 has an Effective Elastic Value of at least 30 mm., particularly at least about 40 mm., and more particularly at least about 50 mm., for improved performances. The effectiveness of the elastic members 46 of an absorbent pad 20 can be determined by an Effective Elastic Value derived from an Effective Elastic Test. The test measures the effectiveness of the elastic members 46 of a folded pad 20 at maintaining the bucket shape for leakage protection without wrinkling or bunching the absorbent assembly 32 (or absorbent core 33) after having been maintained in a folded condition. In general, a side flap 40, in accordance with the present invention, is considered to be effective if the elastic members 46 pulls the side flap 40 up and curves the pad 20 when the pad 20 is unfolded. (See FIG. 13.) The interaction of the elastic members 46 of the side flap 40 with the absorbent assembly 32 (or absorbent core 33) causes a controlled flexure of the absorbent assembly 32 (or absorbent core 33) wherein the end edges 26 and 27 of the absorbent pad 20 are pulled toward each other. This configuration of the end edges 26 and 27 in combination with the side flaps 40 pulled up by the elastic members 46 form a bucket shaped device. If the elastic members 46 just bunch the absorbent assembly 32 (or absorbent core 33) or lay flat against the body-facing surface 34 of the pad 20, the bucket shape is lost. Side flaps 40 that include ineffective elastic members 46 do not provide the gasketing to the body of the wearer and increases leakage or fluid run-off from the side of the absorbent pad 20.

Figure 12:
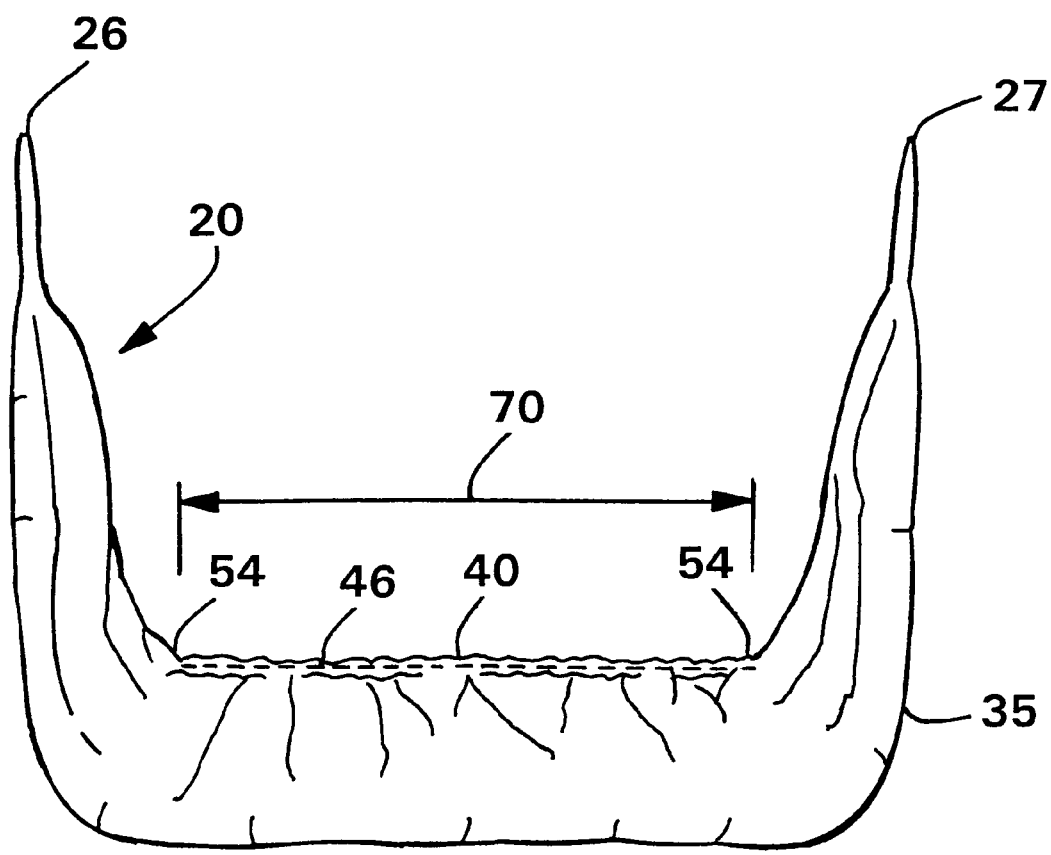
FIG. 12 representatively shows a longitudinal side view of the absorbent pad of FIG. 1, taken along line 2—2 showing the pad and the side flaps in a relaxed configuration.

The Effective Elastic Value test method is used to determine how much the elastic members 46 are elongated or stretched out during the use of the absorbent pad 20. The amount or value of elongation of the elastic members 46 represents the effectiveness of the side flaps 40 of the absorbent pad 20 to remain erect and function as fluid dams during use. This test method, in general, measures the effectiveness of elastic materials in absorbent pad or guard products forming or having a bucket shaped structure. This effectiveness is called Effective Elastic Value, also referred to as the "EEV". The EEV of the elastic material is calculated by subtracting the relaxed length of an elasticized portion (see FIG. 12) of the absorbent pad or guard from the length of that elasticized portion when the pad or guard is unfolded (see FIG. 13), thereby extending the elastic material as the elastic material would be extended during use of the absorbent product when the bucket shaped structure is formed by the side flaps. The EEV can be expressed as the value of the extended length (mm) of an elasticized portion minus the value of the relaxed length of the same elasticized portion of an absorbent product 20 when the pad 20 is unfolded.

The Effective Elastic Value is calculated by subtracting a relaxed or folded elastic length 70 from an unfolded or extended elastic length 72. See FIGS. 12 and 13. The pad 20 to be tested is removed from its pouch, if any, without being unfolded. Place the garment-facing side 35 of the central portion of the pad 20 toward a level bench top. Let the pad 20 open naturally. The pad 20 will not lie flat on the bench top, but rather will assume a "U" or "V" shaped configuration as the end edges 26 and 27 are pulled toward each other by the elastic members 46. (See FIG. 12.) With a permanent marker, for example a SANFORD® Ultra Fine Point SHARPIE®, mark the active ends 54 of the contracted elastic member 46 on both sides 28 and 29 of the pad 20. The active ends 54 of the elastic member 46 can be identified at the point where the smooth portion of the side flap 40 meets the gathered portion of the side flap 40. The side flap 40 gathers where the elastic member 46 interacts with the side flap 40. With a cloth tape measure, measure the distance between the marks on each side flap 40 making sure that the tape measure conforms as closely as possible to the curvature of the elastic member 46 in the pad 20. Record this distance as relaxed elastic length 70.

Unfold the pad by placing a 100 gram weight 64, for example a 3.8 by 5.1 by 1.9 cm. (1.5 by 2.0 by 0.75 inch) aluminum block, on the very end of the absorbent assembly 32 (or absorbent core 33) and with another 100 gram weight 64, push the opposite end of the absorbent assembly 32 (or absorbent core 33) toward the bench until the pad ends 26 and 27 are both on the bench surface. (See FIG. 13.) Do not smooth out or stretch the center of the pad 20. Allow the absorbent assembly 32 (or absorbent core 33) of the pad 20 to interact with the elastic members 46 without interference. If the absorbent assembly 32 (or absorbent core 33) of the pad 20 has a tendency or propensity to buckle, bunch, or wrinkle, do not prevent such a reaction or effect. Again measure the distance between the marks on the active ends 54 of the elastic members 46 and record as the extended or unfolded elastic length 72.

Subtract the corresponding relaxed elastic lengths 70 from the extended or unfolded elastic lengths 72. Calculate the average and standard deviation for 15 sample pads, with one measurement per side. The average represents the Effective Elastic Value.

By having the elastic members 46 located above the plane of the absorbent assembly 32 (or absorbent core 33), the elastic members 46 tend to curve the absorbent pad 20 into a desirable bucket shape as opposed to simply bunching the pad 20 together. The absorbent assembly 32 (or absorbent core 33) of the present invention is specifically designed to not to buckle, bunch, or wrinkle (or significantly reduce buckling, bunching, or wrinkling). The body-facing surface 34 of the absorbent pad 20 thus tends to exhibit a smooth, non-bunched surface, which is more desirable for fluid absorption and comfort.

The buckling, bunching, or wrinkling (the gibbosity) of the absorbent assembly 32 (or absorbent core 33) can be measured using a surface topographic method. The pad 20 to be tested is removed from its pouch, if so packaged. The peel-strip is removed from the garment attachment adhesive 60 (discussed below). The garment-facing side 35 of the pad 20 is pressed down onto a 10 inch by 12 inch glass plate 80, using the garment attachment adhesive 60 to adhere the pad 20 to the glass plate 80. (See FIG. 14.) The topsheet layer 31 (the material acting as the body side liner or cover) is coated by brush application with a 1:1 solution of white Pentel® Correction Fluid (commercially available from the Pentel of Americas, LTD company located in Torrance, Calif.) and n-butanol to create an opaque surface for shadow projection. Typically, a coating of a few tenths of a micron in thickness results. The pad 20 is allowed to dry overnight. This is necessary because of the absorption of the coating solution into the pad 20.

Figure 14:
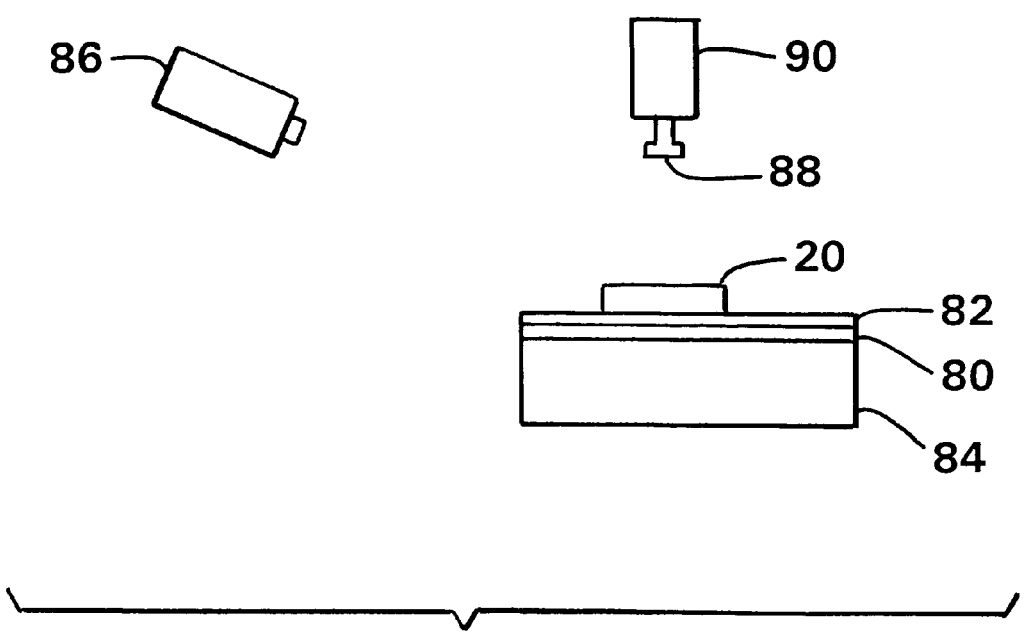
FIG. 14 representatively shows a schematic representation of the apparatus used to measure the Gibbosity Factor.

The plate glass 80 with the pad 20 mounted on it is placed on a 12 inch by 12 inch auto-macrostage 84 covered with poster-board 82, typically between 1/16 inch to 1/8 inch in thickness to protect the auto-macrostage from scratching. The auto-macrostage is commercially available from the Design Components, Inc. located in Franklin, Mass. The pad 20 is illuminated with a light source 86, such as a slide projector, in a fixture that allows the light beam to be projected at an angle of 30 degrees from horizontal, wherein horizontal is defined as the surface on which the pad is mounted as shown in FIG. 14. The light beam from the light source 86 produces clear high-contrast shadows behind the wrinkles in the absorbent assembly 32 (or absorbent core 33) when viewed through a lens 88, such as a 50 mm El-Nikkor lens at f/4. The 50 mm El-Nikkor provides a 2.25 inch field-of-view.

Figure 15:
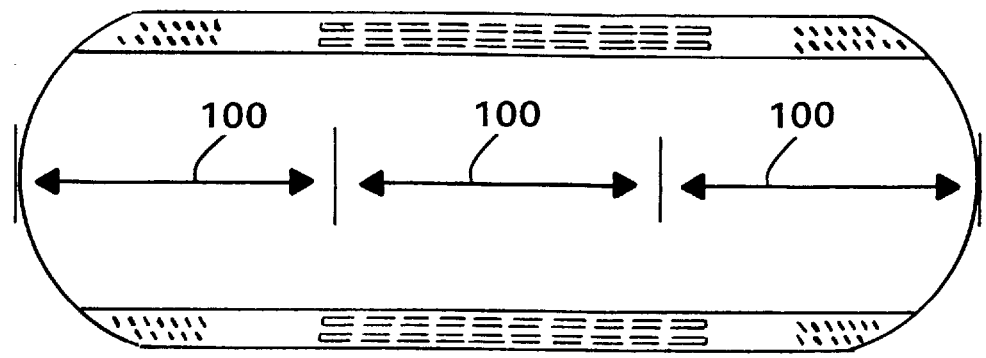
FIG. 15 representatively shows a top plan view of the absorbent pad of FIG. 1, taken from the body-facing side of the pad and in a stretched and laid flat condition showing fields-of-view used to evaluate the pad.
Figure 16:
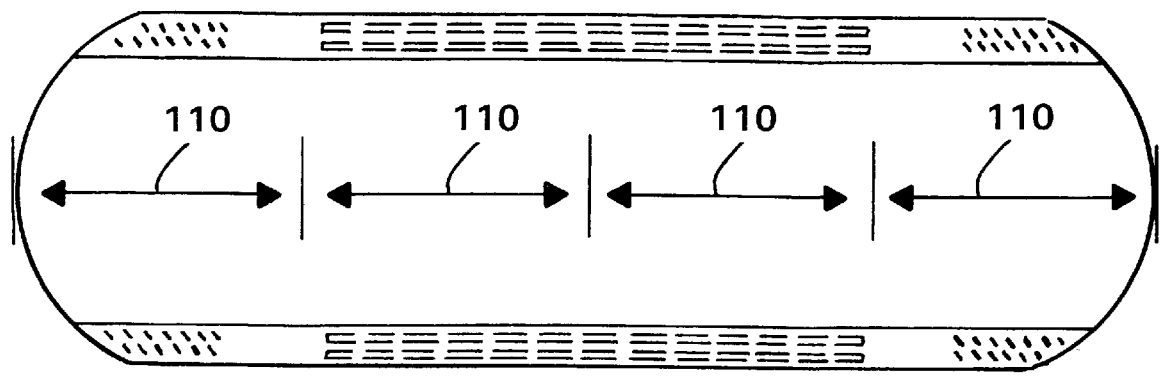
FIG. 16 representatively shows a top plan view of the absorbent pad of FIG. 1, taken from the body-facing side of the pad and in a stretched and laid flat condition showing fields-of-view used to evaluate the pad.

The wrinkles are detected and evaluated as "line slices" using the multi-frame capacity of an image analysis system. Generally, four fields-of-view (each field-of-view is approximately 2¼ inches in length) are used to cover the entire length of the pad being evaluated. On a shorter pad, only 3 fields-of-view are required to evaluate the entire surface of the pad. The fields-of-view taken on a shorter pad are represented by lines 100 as shown in FIG. 15. The fields-of-view taken on a longer pad are represented by lines 110 as shown in FIG. 16. Such an image analysis system is the Leica/Cambridge Quantimet 900 Image Analysis System commercially available from the Leica, Inc. located in Deerfield, Ill. The 900 Image Analysis System is used with a scanner 90, such as a Newvicon scanner also available from the Leica, Inc.

The image analysis system provides indexing of the stage from field to field. The stage itself rests upon the base of a Kreonite Mobile Studio commercially available the J. Kelly Associates located in Darien, Ill. The analysis is completed using the WRINK2 software program written in the macro programing language, QUIPS, provided with the Leica/Cambridge Quantimet 900 Image Analysis System. Using the routine as follows:

```
NAME=WRINK2
DOES=Optical crepe analysis providing two histograms:
    One on PEAK HT; the other on PEAK-TO-PEAK distance.
AUTH=name of tester
DATE=day month year
Enter specimen identity
Scanner      (No. 2 Newvicon LV=0.00 SENS=1.64)
Load Shading Corrector (pattern - BEHNKE)
Calibrate User Specified (Calibration Value =0.06689 millimetres per pixel)*
CALL STANDARD
NO              :=0.
NO              :=18.
TANTHETA        :=0.
TANTHETA        :=0.57735
LTRAMECNT       :=0.
Stage Scan      (         X         Y
    Scan origin    15000.0    25000.0
```

-continued

```
   Field size    9600.0      4000.0
   No of fields      4       1 )**
Detect 2D      (Darker than 24 PAUSE)
For FIELD
FRAMEPOSX :=0.
FRAMEPOSY :=0.
XPOS          :=70.
YPOS          :=50.
Scanner    (No. 2 Newvicon AUTO-SENSITIVITY LV=0.00)
Live Frame is multiple Rectangle (X: 48, Y: 36, W:800, H: 128, )
Image Frame is multiple Rectangle (X:XPOS   , Y:YPOS   , W:750, H:   10, )
Detect 2D    (Darker than 24)
Amend    (OPEN by 2)
Amend    (OPEN by 8 - Horizontally)
Amend    (DILATE by 1 - Vertically)
Measure feature   AREA      FERET 0     FERET 90
   Into array FEATURE (of 700 features and 4 parameters)
FEATURE CALC       :=TENTHETA*AREA/FERET 90
Distribution of COUNT v CALC from FEATURE in HISTO1
   From 0.10 to 10.00 in 15 bins (LOG)
Amend     (SKELETON - Sub mode=Peel Ends)
Amend     (DILATE by 10 - Vertically)
Image Transfer from Invert A to Binary Output
Measure feature   AREA     FERET 0      FERET 90
   Into array FEATURE (of 600 features and 4 parameters)
FEATURE CALC       :=AREA/FERET90
Distribution of COUNT v CALC from FEATURE in HISTO2
   From 0.10 to 100.00 in 15 bins (LOG)
LFRAMECNT :=LFRAMECNT+1.
Stage Step
Next FIELD
Print ""
Print "PEAK HEIGHT HISTOGRAM (UM) ------"
Print Distribution (HISTO1, differential, bar chart, scale=   0.00)
Print ""
Print ""
Print "VALLEY DISTANCE HISTOGRAM (UM)----"
Print Distribution (HISTO2, differential, bar chart, scale=   0.00)
Print ""
Print "TOT SCAN LENG=", LFRAMECNT*NO*CAL.CONST*I.FRAM.WR," MM"
Print ""
Print "TOT # OF FIELDS =", FIELDNUM,"  DETECTION =" , DET.LOWER
For LOOPCOUNT=1 to   4
Print ""
Next
End of Program
```

*NOTE - Calibrations values will vary slightly depending on actual camera and optics.
**NOTE - Number of fields for short pads equals 3.

Various measures are taken of wrinkle intensity, such as the count of peaks (line-slice length) per field and mean peak height. Similar procedures have been used in image analysis for tissue as discussed in the following U.S. Pat. Nos.: 5,667,635; 5,411,636; and, 5,722,968, the entire disclosures of which are hereby incorporated by reference in a manner that is consistent herewith. The measures taken are used to determine the Gibbosity Factor.

To further define the interaction between the absorbent assembly 32 (or absorbent core 33) and the side flaps 40, the Gibbosity Factor needs to be considered. For the bucket shaped structure to be formed within the pad 20, the side flaps 40, through the application of the elastic members 46 that are at least partially out of the plane of the absorbent assembly 32 (or absorbent core 33), pull the end edges 26 and 27 of the pad 20 upward, toward each other. This is accomplished in the present invention as the side flaps 40 interact with the end edges 26 and 27 of the pad 20 and not with buckling, bunching, or wrinkling of the absorbent assembly 32 (or absorbent core 33) due to the structure and stiffness of the absorbent assembly 32 (or absorbent core 33). The more the absorbent assembly 32 (or absorbent core 33) wrinkles or otherwise deforms when acted upon by the side flaps 40, the less the side flaps 40 interact with the end edges 26 and 27. The less the side flaps 40 interact with the end edges 26 and 27 to form the bucket, the less the side flaps 40 remain above the plane, reducing the volume of bodily fluid and semi-fluid discharge that the formed bucket will hold, thereby resulting in increased leakage.

The Gibbosity Factor is the product of the number of peaks (buckles, bunches, wrinkles, ect.) that are formed within the absorbent assembly 32 (or absorbent core 33) when the absorbent assembly 32 (or absorbent core 33) interacts with elastic materials such as the elastic members 46 within the side flaps 40 and the average height of the peaks. The Gibbosity Factor represents the amount of deformation due to wrinkling type activity. The greater the Gibbosity Factor, the less likely a product will be able to form a bucket shaped structure as does the pad 20 of the present invention. The Gibbosity Factor is preferably less than about 18, more preferably less than about 15, and most preferably less than about 12.

The following formula is used to calculate the Gibbosity Factor:

$g=[p][h]$ wherein g=Gibbosity Factor p=peak count h=average peak height in mm units The absorbent pad 20 also includes a means for holding the pad 20 in position during use. In the illustrated embodiment, garment attachment means such as garment attachment adhesive 60 is disposed on the backsheet layer 30 remote from the absorbent assembly 32 (or absorbent core 33). The garment attachment adhesive 60 is desirably located transversely inward of the proximal edges 48 of the side panel members 42 and 44. A peel strip 62 of release paper may be releasably bonded to the garment attachment adhesive 60 prior to use. Other garment attachment means such as mechanical fasteners, for example hook-and-loop fasteners, body attachment adhesive, wings, or the like may alternatively be used to hold the absorbent pad 20 in position relative to the undergarment or the wearer.

Performance of absorbent pads 20 of the present invention can be improved by incorporating a feature referred to herein as anti-roll back. The term "anti-roll back" is used to refer to an interrelation of components that minimizes the tendency of the end edges 26 and 27 of the absorbent pad 20 to roll up on themselves due to the effectiveness of the elastic members 46. More specifically, the garment attachment adhesive 60 is positioned and extends longitudinally outward of the active ends 54 of the elastic members 46 and longitudinally inward of the respective longitudinal end edges 26 and 27 of the absorbent pad 20. This particular feature allows the end edges 26 and 27 of the absorbent pad 20 to resist rolling back onto the body-facing surface 34 of the pad 20. The garment attachment adhesive 60 is desirably positioned and extends longitudinally outward of the lines of elastic retraction force emanating from the active ends 54 of the elastic members 46.

Roll-back of the end edges 26 and 27 of the absorbent pad 20 tends to occur with effective elastic members 46 because the elastic members 46 in the side flaps 40 pulls the end edges 26 and 27 of the pad 20 and rolls the end edges 26 and 27 toward the transverse centerline 24 of the pad 20. Roll-back creates an uncomfortable lump as the absorbent assembly 32 (or absorbent core 33) is doubled up. Roll-back also pulls the garment attachment adhesive 60 loose from the underwear which, when free of the underwear, can stick to skin and hair causing irritation and pain for a wearer.

The components of the absorbent pad 20 may be bonded together using ultrasonic bonds, thermal bonds, adhesives, or other suitable means. The term "bonded" refers to the joining, adhering, connecting, attaching, or the like, of two elements. Two elements will be considered to be bonded together when they are bonded directly to one another or indirectly to one another, such as when each is directly bonded to intermediate elements.

Figure 11:
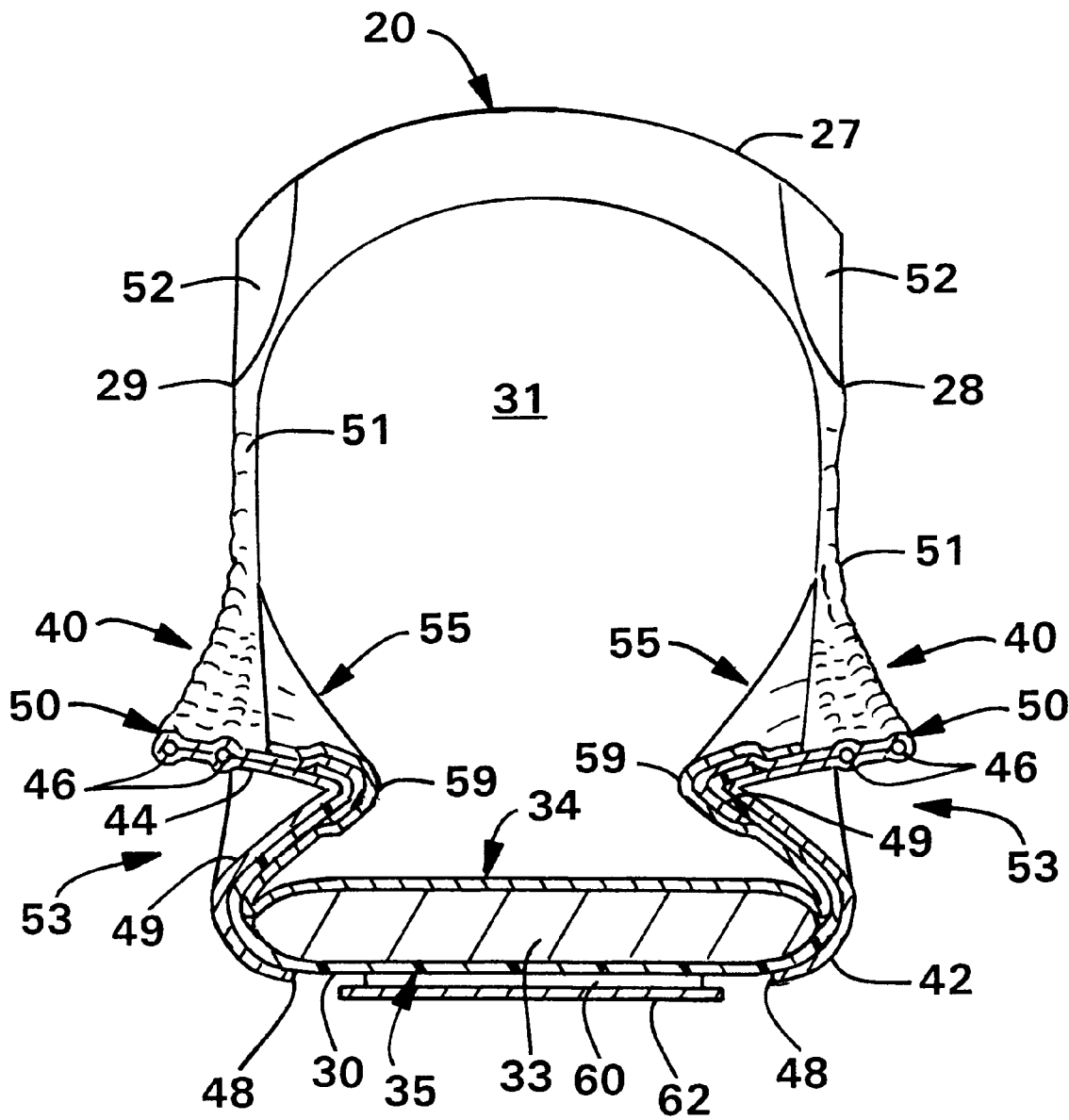
FIG. 11 representatively shows a top plan view of the absorbent pad of FIG. 1, taken from the body-facing side of the pad and in a stretched and laid flat condition showing a folded configuration of the side flaps, with portions broken away for purposes of illustration.

The present invention further comprises an absorbent pad 20 wherein the side flaps 40 are folded during use prior to an insult of fluid on the dry absorbent pad 20. As illustrated in FIG. 11, the garment-facing surface 35 of each side flap 40 folds back onto itself, forming an accordion pleated structure 53. The body-facing region 55 on each folded side flap 40 has gasketing characteristics, maintaining a gasketing contact relationship between the absorbent pad 20 and the body of the wearer. The side flaps 40 act as a barrier, preventing fluid escaping off the side edges 28 and 29 of the absorbent pad 20 during heavy or multiple insults of fluid.

After at least an initial insult of fluid, the absorbent assembly 32 (or absorbent core 33) shifts as the fluid is absorbed. The side flaps 40 at least partially unfold to accommodate the shifting of the absorbent assembly 32 (or absorbent core 33), thereby maintaining the gasketing contact relationship between the body of the wearer and the absorbent pad 20. The side flaps 40 may completely unfold under multiple insults or heavier loading of fluid, continuing to maintain the gasketing contact relationship between the body of the wearer and the absorbent pad 20. As the weight of the fluid causes the absorbent pad 20 to move downward, the side flaps 40 unfold, maintaining the gasketing contact relationship between the pad 20 and the wearer's body.

In other embodiments, the component (not shown) having gasketing characteristics may comprise any flexible materials along the longitudinal side edges 28 and 29 of the pad 20. The flexible material may also comprise elasticized flaps, non-recovery stretchable material, or a coil of material that unwraps with the weight of the absorbent assembly 32 or absorbent core 33. Each component includes a proximal edge 48 disposed on the garment-facing surface 35 of the absorbent pad 20 and a distal edge 49 disposed outwardly of the proximal edge 48 defining a free edge 51 of the component. Prior to the insult of fluid, the component is folded, or accordion pleated while maintaining a gasketing contact relationship between the body of the wearer and the absorbent pad 20. The component forms a barrier having gasketing characteristics that retains the fluid of each insult until the fluid has been absorbed.

After at least an initial insult of fluid, the absorbent assembly 32 (or absorbent core 33) shifts as the fluid is absorbed. The component at least partially unfolds to accommodate the shifting of the absorbent assembly 32 (or absorbent core 33), thereby maintaining the gasketing contact relationship between the body of the wearer and the absorbent pad 20. The component may completely unfold under multiple insults or heavier loading of fluid, continuing to maintain the gasketing contact relationship between the body of the wearer and the absorbent pad 20.

The present invention provides an absorbent pad 20 having gasketing characteristics, thereby maintaining contact between the absorbent pad 20 and the wearer's body whether the pad 20 is dry or has been insulted with fluid. The effectiveness of the side flaps 40 or gasketing components is observed in video data and image capture photography with the use of the OLYMPUS® video imagescope (VIS) system which includes a video analyzer. VIS uses a small video camera in a flexible insertion tube with various lens options to facilitate imaging.

During a study of commercially available absorbent pads during simulated use, it was discovered that the thickness of the absorbent assembly or absorbent core consisting of cellulose fibers and super absorbent materials increases with fluid instillation. This change reduced the effective gasketing characteristics of the commercially available absorbent pads. In some of the absorbent pads, the absorbent assembly or core swells upward, creating a bulge in the center of the absorbent assembly or core, and pushes the gasketing component away from the body of the wearer. In other instances, the weight of the fluid pulls the absorbent pads away from the wearer's body, breaking the gasketing contact between the wearer's body and the gasketing component.

Figure 3:
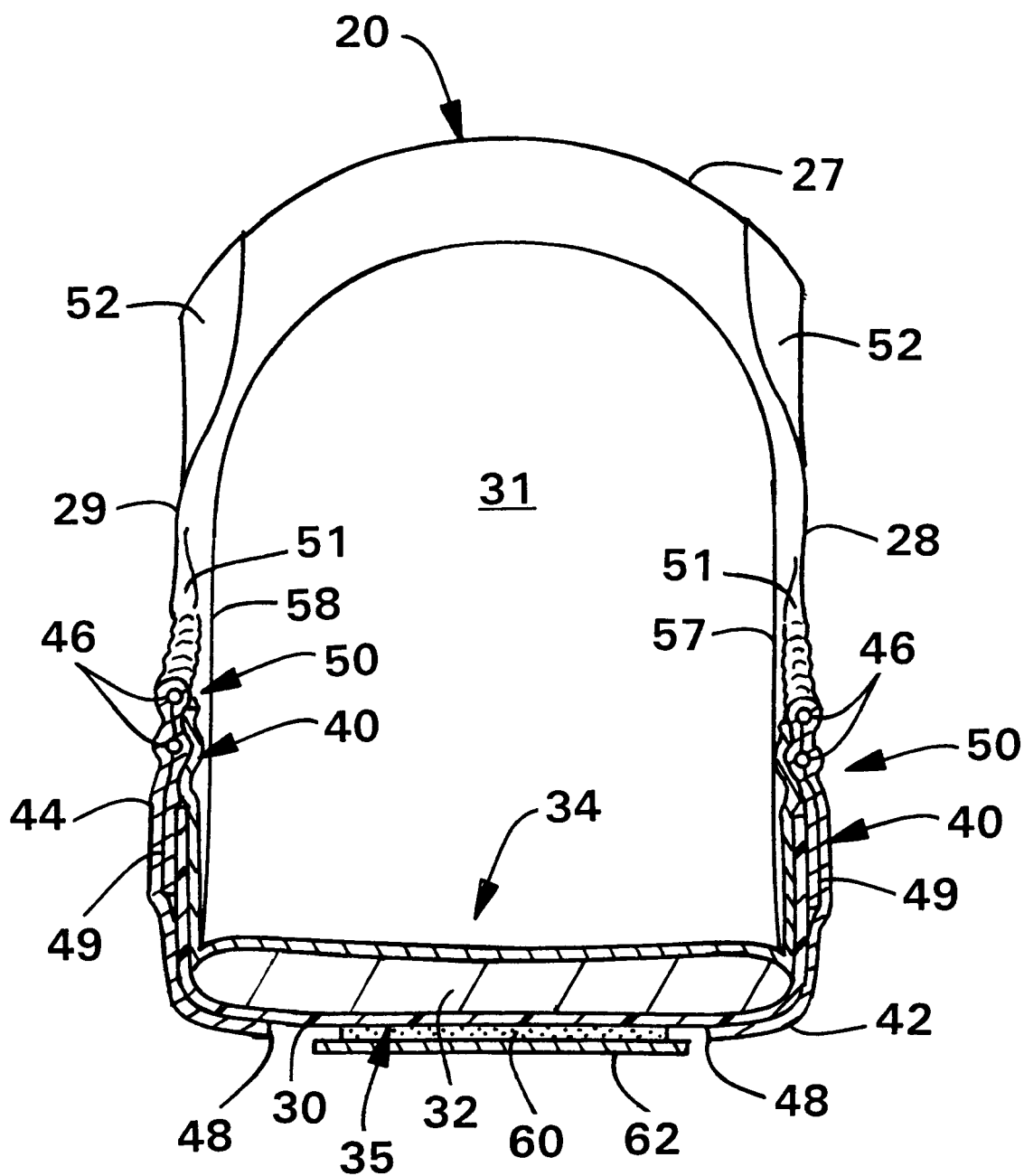
FIG. 3 representatively shows a transverse section view taken along line 3—3 of FIG. 1.
Figure 8:
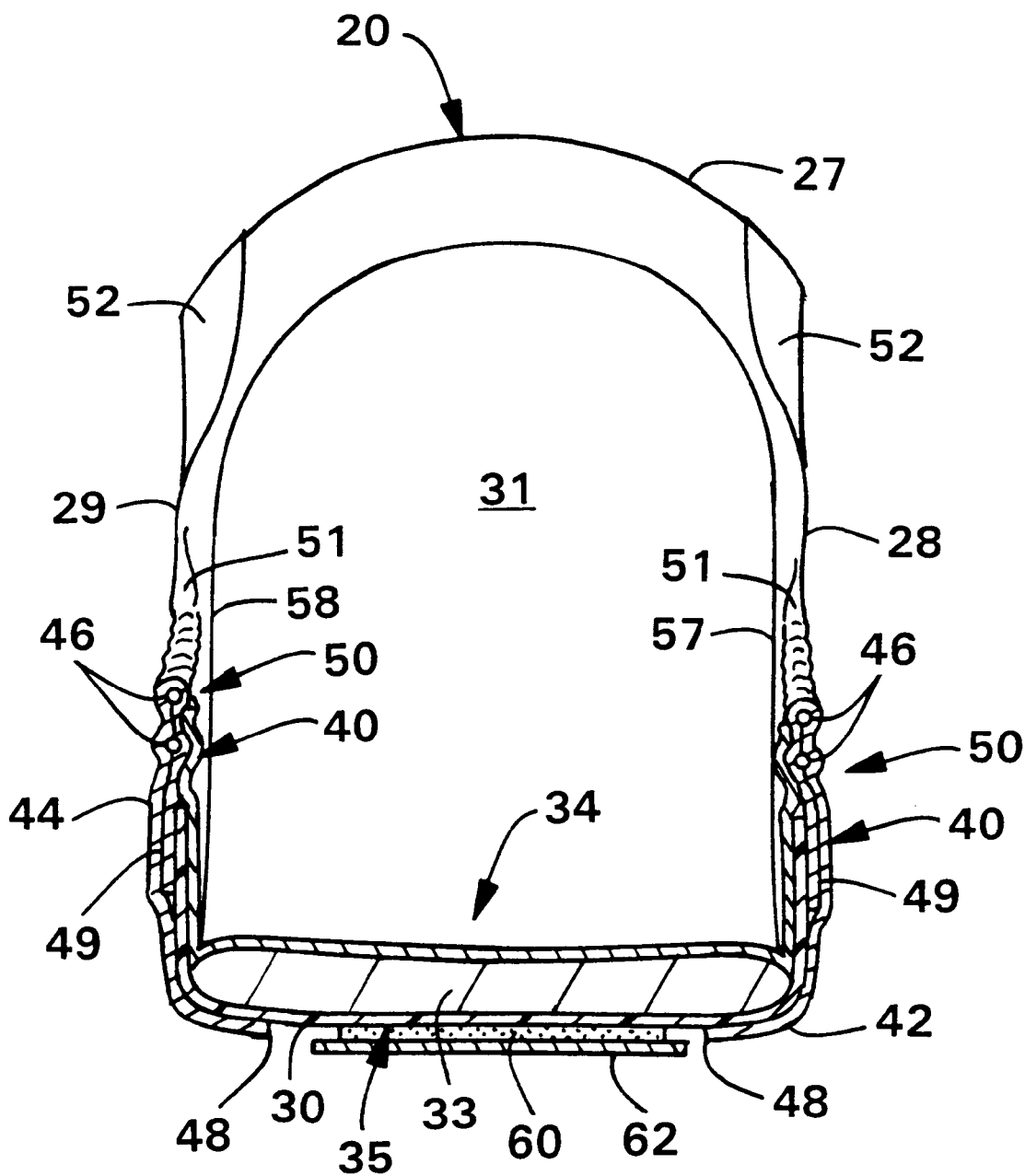
FIG. 8 representatively shows a transverse section view taken along line 3—3 of FIG. 1.

VIS showed the folded or accordion pleated structure 53 of the side flaps 40 of the dry, prior to an insult of fluid, absorbent pad 20. VIS also showed the gasketing contact between the wearer's body and the dry absorbent pad 20. The body-facing region 55, defined by the folding of the side flaps 40, provides a gasketing contact between the wearer's body and the absorbent pad 20. After at least one insult of fluid, the side flaps 40 at least partially unfolded while maintaining a gasketing contact relationship between the wearer's body and the absorbent pad 20. After multiple insults of fluid or heavier loading, the side flaps 40 completely unfolded while continuing to maintain the gasketing contact between the wearer's body and the pad 20. The configuration of the unfolded side flaps 40 is illustrated in FIGS. 3 and 8.

The position and configuration of the side flaps 40 of the pad 20 during use prior to, during, and after multiple insults of fluid were observed using the VIS technology. Each wearer wore body hugging tights. A body hugging mesh panty containing a wetting apparatus was placed over the tights. The wetting apparatus is designed to simulate an insult of fluid such as occurs during an incontinence episode. The wearer then put on an appropriate sized pair of Fruit of the Loom® panty styled underwear including a properly placed absorbent pad 20.

The pad 20 was marked with a permanent marker, for example a SANFORD® Ultra Fine Point SHARPIE®, to aid visual differentiation of specific components of the pad 20. Another color was used to mark the free edge 51. Another color was used to mark the longitudinal side edges 57 and 58 of the absorbent assembly 32 (or absorbent core 33) of the pad 20. Another color was used to mark the inner fold edge 59 defined by the folded side flap 40. (See FIG. 11). The longitudinal and transverse axes 22 and 24 were marked in different colors as well. All of these components of the absorbent pad 20 could have been marked with the same color, however, it would be more difficult to differentiate the components during the simulated use tests. To further aid visualization in the tests, tights and underwear of different colors, differing from the colors of the markers as well as from each other, were used.

A lighted fiber-optic camera (VIS) was then inserted between the tights and the absorbent pad 20, allowing visualization of the pad 20 during the simulated use tests. The design of the VIS system has minimal or no intrusive effects on the function of the pad and the simulated incontinence tests.

The observations of the dry pad 20 showed that the side flaps 40 defined a folded or accordion pleated structure 53 during use. It was further observed that the body-facing region 55 of the accordion pleated structure 53 maintained a gasketing contact relationship between the wearer's body and the absorbent pad 20.

Insults of saline of varying amounts were added to the absorbent pad 20 at various time intervals through the wetting apparatus. The saline was blue-tinged to improve the conditions under which the observations were taken. The side flaps 40 and the gasketing characteristics of the pad 20 were observed both during each insults and after each insult. After at least one insult, the side flaps 40 at least partially unfolded while maintaining the gasketing contact relationship between the wearer's body and the absorbent pad 20. The amount of unfolding displayed by the side flaps 40 depended on the number and/or volume of the insults introduced to the absorbent pad 20. In several instances, under multiple insults or heavy loading of the absorbent pad 20, the side flaps 40 unfolded completely while continuing to maintain the gasketing contact relationship between the wearer's body and the absorbent pad 20.

In one embodiment of the present invention, the absorbent pad 20, defining longitudinal and transverse axes 22 and 24, comprises a backsheet layer 30; a fluid permeable topsheet layer 31 superposed on the backsheet layer 30; an absorbent assembly 32 sandwiched between the backsheet layer 30 and the topsheet layer 31; and, side flaps 40 disposed transversely outward of the absorbent assembly 32. Each side flap 40 comprising an elastic member 46 that is at least partly out of the plane of the absorbent assembly 32 when the absorbent pad 20 is in a generally flat position. In addition, each side flap 40 maintains a gasketing contact relationship with a wearer's body during use. The absorbent pad 20 may have a Gurley stiffness greater than about 2000 milligrams.

The side flaps 40 of the absorbent pad 20 are folded during use prior to an insult of fluid on the absorbent pad 20. The side flaps 40 at least partially unfold during use after at least one insult of fluid on the absorbent pad 20. The side flaps 40 may unfold completely during use after at least one insult of fluid on the absorbent pad 20.

In another embodiment of the present invention, the absorbent pad 20, defining longitudinal and transverse axes 22 and 24, comprises a backsheet layer 30; a fluid permeable topsheet layer 31 superposed on the backsheet layer 30; a single layer absorbent core 33 sandwiched between the backsheet layer 30 and the topsheet layer 31; and, side flaps 40 disposed transversely outward of the absorbent core 33. Each side flap 40 comprising an elastic member 46 that is at least partly out of the plane of the absorbent core 33 when the absorbent pad 20 is in a generally flat position. In addition, each side flap 40 maintains a gasketing contact relationship with a wearer's body during use. The absorbent pad 20 may have a Gurley stiffness of at least about 800 milligrams.

The side flaps 40 of the absorbent pad 20 are folded during use prior to an insult of fluid on the absorbent pad 20. The side flaps 40 at least partially unfold during use after at least one insult of fluid on the absorbent pad 20. The side flaps 40 may unfold completely during use after at least one insult of fluid on the absorbent pad 20.

In another embodiment of the present invention, the absorbent pad 20, defining a longitudinal axis 22, a transverse axis 24, opposite longitudinal end edges 26 and 27, and opposite longitudinal side edges 28 and 29 extending between the longitudinal end edges 26 and 27. The absorbent pad 20 comprises a backsheet layer 30; a fluid permeable topsheet layer 31 superposed on the backsheet layer 30; an absorbent assembly 32 sandwiched between the backsheet layer 30 and the topsheet layer 31; side flaps 40 disposed transversely outward of the absorbent assembly 32 comprising an proximal edge 48, a distal edge 49, a body-facing surface 34 which is configured to be in a contacting relationship with a wearer's body during use, at least one elastic member 46 having opposite active ends 54 that are longitudinally spaced from the respective longitudinal end edges 26 and 27 of the absorbent pad 20, wherein the proximal edge 48 is attached to the longitudinal side edges 28 and 29 of the absorbent pad 20, and at least adjacent the elastic members 46, the distal edge 49 remains unattached from the longitudinal side edges 28 and 29 of the absorbent pad 20; and garment attachment means disposed on the backsheet layer 30 remote from the absorbent assembly 32, the garment attachment means positioned and extends longitudinally outward of the active ends 54 of the elastic members 46. The absorbent pad 20 has an Effective Elastic Value of at least 30 millimeters.

The side flaps 40 of the absorbent pad 20 are folded during use prior to an insult of fluid on the absorbent pad 20. The side flaps 40 at least partially unfold during use after at least one insult of fluid on the absorbent pad 20. The side flaps 40 may unfold completely during use after at least one insult of fluid on the absorbent pad 20.

In another embodiment of the present invention, the absorbent pad 20, defining a longitudinal axis 22, a transverse axis 24, opposite longitudinal end edges 26 and 27, and opposite longitudinal side edges 28 and 29 extending between the longitudinal end edges 26 and 27. The absorbent pad 20 comprises a backsheet layer 30; a fluid permeable topsheet layer 31 superposed on the backsheet layer 30; a single layer absorbent core 33 sandwiched between the backsheet layer 30 and the topsheet layer 31; side flaps 40 disposed transversely outward of the absorbent core 33 comprising an proximal edge 48, a distal edge 49, a body-facing surface 34 which is configured to be in a contacting relationship with a wearer's body during use, at least one elastic member 46 having opposite active ends 54 that are longitudinally spaced from the respective longitudinal end edges 26 and 27 of the absorbent pad 20, wherein the proximal edge 48 is attached to the longitudinal side edges 28 and 29 of the absorbent pad 20, and at least adjacent to the elastic members 46, the distal edge 49 remains unattached from the longitudinal side edges 28 and 29 of the absorbent pad 20; and garment attachment means disposed on the backsheet layer 30 remote from the absorbent core 33, the garment attachment means positioned and extends longitudinally outward of the active ends 54 of the elastic members 46. The absorbent pad 20 has an Effective Elastic Value of at least 30 millimeters.

The side flaps 40 of the absorbent pad 20 are folded during use prior to an insult of fluid on the absorbent pad 20. The side flaps 40 at least partially unfold during use after at least one insult of fluid on the absorbent pad 20. The side flaps 40 may unfold completely during use after at least one insult of fluid on the absorbent pad 20.

EXAMPLES

Having thus described the present invention and the process for making it, a series of examples were prepared to give a more detailed understanding of the invention. The particular amounts, proportions, compositions and parameters are meant to be exemplary, and are not intended to specifically limit the scope of the invention.

Example 1

An absorbent pad of the type illustrated in FIGS. 1–5 was constructed and is designated as Example 1 in TABLE 1. The absorbent pad comprised a backsheet layer formed of a 0.028 mm. thick polyethylene film. An absorbent assembly of the type illustrated in FIG. 6 was disposed on the backsheet layer, and a topsheet layer was disposed on the absorbent assembly. The topsheet layer comprised a surfactant treated spunbond web of side-by-side bicomponent filaments with 50 percent polyethylene and 50 percent polypropylene having a basis weight of about 20 gsm.

The absorbent assembly comprised a fluid storage layer and an acquisition/distribution layer. The storage layer was formed of an air-laid mixture of 470 gsm wood pulp fibers and 305 gsm high-absorbency materials that was sandwiched between a pair of 19 gsm cellulose tissues. The storage layer was embossed using a matched male/male embossing roll. The acquisition/distribution layer comprised a through-air bonded carded web composed of a blend of 40 percent 6 denier polyester fibers and 60 percent 3 denier polypropylene/polyethylene side-by-side bicomponent fibers, with an overall basis weight of about 120 gsm. The storage layer was hourglass shaped and the acquisition/distribution layer was rectangular.

The absorbent pad included side flaps that extended along the full length of the side edges of the pad. The longitudinal ends of the side flaps were folded and bonded to themselves. As shown in FIGS. 1–5, the side flaps were formed by lateral portions of both the backsheet layer and the topsheet layer, and by portions of two separate side panel members. The side panel members comprised a high loft, fuzzy nonwoven spunbond made of side-by-side bicomponent filaments of 50 percent polyethylene and 50 percent polypropylene. The side panel members included folded regions that enclosed two 720 denier elastomeric threads. The threads were stretched 160 percent of their original length and operatively joined to the side panel members with a hot melt adhesive over a distance of 16.5 cm.

The Gurley stiffness values of ten absorbent pads were measured. The pads had an average Gurley stiffness of 1438 mg. at one end, with a standard deviation of 222 mg., and 1336 mg. at the other end, with a standard deviation of 269 mg.

Example 2

Another absorbent pad designated as Example 2 in TABLE 1 was constructed. The absorbent pad was similar to that of Example 1 except that the storage layer was embossed more aggressively.

The Gurley stiffness values of ten absorbent pads of Example 2 were measured. The pads had an average Gurley stiffness of 4,525 mg. at one end, with a standard deviation of 1372 mg., and 3,253 mg. at the other end, with a standard deviation of 1145 mg.

For purposes of comparison, absorbent pads designated Examples 3–11 were purchased and their Effective Elastic Value and the Elastic Out Of The Plane Value were measured.

Example 3 (Comparative)

POISE Extra Plus Absorbency pads manufactured by Kimberly-Clark Corporation were purchased in or near Appleton, Wis. on Oct. 15, 1996.

Example 4 (Comparative)

KOTEX Secure Hold Maxi pads manufactured by Kimberly-Clark Corporation were purchased in or near Appleton, Wisc. on Oct. 15, 1996.

Example 5 (Comparative)

KOTEX Curved Maxi pads manufactured by Kimberly-Clark Corporation were purchased in or near Appleton, Wis. on Oct. 15, 1996.

Example 6 (Comparative)

ATTENDS guards manufactured by The Procter & Gamble Company were purchased in or near Appleton, Wis. on Oct. 15, 1996.

Example 7 (Comparative)

ATTENDS pads manufactured by The Procter & Gamble Company were purchased in or near Appleton, Wis. on Oct. 15, 1996.

Example 8 (Comparative)

ALWAYS Curved Maxi with side gathers manufactured by The Procter & Gamble Company were purchased in or near Appleton, Wis. on Oct. 15, 1996.

Example 9 (Comparative)

CERTINA Super pads were purchased in Europe in 1995. The Effective Elastic Value and the Elastic Out Of The Plane Value are based on measurements from 6 rather than 15 pads.

Example 10 (Comparative)

SERENITY STAYFREE Extra Plus pads manufactured by Johnson & Johnson were purchased in or near Appleton, Wis. on Oct. 5, 1996.

Example 11 (Comparative)

CUC Ultra Plus pads were purchased in or near Appleton, Wis. on Oct. 15, 1996.

The Effective Elastic Value and the Elastic Out Of The Plane Value were measured for each of Examples 1–11. The results are presented in TABLE 1 below. For Examples 1 and 2, the pads were folded and stored in a compressed condition for 10 days in order to simulate commercial packaging conditions. The elastics of the Example 1 and Example 2 pads were completely out of the plane of the absorbent assembly. For the pads of Examples 3–11, only the pad of Example 9 was at least partly out of the plane of the absorbent assembly. For the pads of Examples 1–11, only the pads of the present invention (Examples 1 and 2) consistently kept the elastic members out of the plane of the absorbent assembly or absorbent core.

TABLE 1

|         | Effective Elastic Value |           | Elastic Out Of The Plane Value |           |
|---------|-------------------------|-----------|-------------------------------|-----------|
| Example | Average                 | Std. Dev. | Average                       | Std. Dev. |
| 1       | 36.9                    | 9.6       | 4.5                           | 2.1       |
| 2       | 58.5                    | 8.2       | 9.6                           | 2.5       |
| 3       | 5.3                     | 5.8       | −8.3                          | 1.2       |
| 4       | 5.5                     | 1.8       | −6.7                          | 1.0       |
| 5       | 3.7                     | 2.2       | −8.5                          | 1.1       |
| 6       | 8.5                     | 2.7       | −7.6                          | 1.4       |
| 7       | 6.5                     | 4.5       | −5.7                          | 1.3       |
| 8       | 8.8                     | 4.7       | −5.4                          | 1.1       |
| 9       | 25.8                    | 2.0       | −0.3                          | 0.8       |
| 10      | 8.0                     | 3.6       | −4.9                          | 1.0       |
| 11      | 8.5                     | 2.7       | −4.7                          | 1.6       |

Example 12

An absorbent pad of the type illustrated in FIGS. 1–5 was constructed and is designated Example 12. The absorbent pad comprised a backsheet layer formed of a 0.028 mm. thick polyethylene film. An absorbent assembly of the type illustrated in FIG. 6 was disposed on the backsheet layer, and a topsheet layer was disposed on the absorbent assembly. The topsheet layer comprised a surfactant treated spunbond web of side-by-side bicomponent filaments with 50 percent polyethylene and 50 percent polypropylene having a basis weight of about 20 gsm.

The absorbent assembly comprised a fluid storage layer and an acquisition/distribution layer. The storage layer was formed of an air-laid mixture of 470 gsm wood pulp fibers and 305 gsm high-absorbency materials that was sandwiched between a pair of 19 gsm cellulose tissues. The storage layer was embossed using a matched male/male embossing roll. The acquisition/distribution layer comprised a through-air bonded carded web composed of a blend of 40 percent 6 denier polyester fibers and 60 percent 3 denier polypropylene/polyethylene side-by-side bicomponent fibers, with an overall basis weight of about 120 gsm. The storage layer was hourglass shaped and the acquisition/distribution layer was rectangular.

The absorbent pad included side flaps that extended along the full length of the side edges of the pad. The longitudinal ends of the side flaps were folded and bonded to themselves. As shown in FIGS. 1–5, the side flaps were formed by lateral portions of both the backsheet layer and the topsheet layer, and by portions of two separate side panel members. The side panel members comprised a high loft, fuzzy nonwoven spunbond made of side-by-side bicomponent filaments of 50 percent polyethylene and 50 percent polypropylene. The side panel members included folded regions that enclosed two 720 denier elastomeric threads. The threads were stretched 160 percent of their original length and operatively joined to the side panel members with a hot melt adhesive over a distance of 16.5 cm.

The position and configuration of the side flaps the pad were observed prior to, during, and after multiple insults of fluid. The gasketing characteristics of the pad were observed using VIS technology.

For purposes of comparison, absorbent pads designated as Examples 13–16 were purchased and their gasketing characteristics were tested.

Example 13 (Comparative)

POISE Extra Plus Absorbency pads manufactured by Kimberly-Clark Corporation were purchased in or near Appleton, Wis. in 1996. The product, designed with less retention capacity than the present invention, demonstrated good gasketing characteristics in the dry product. However, as the product absorbed the fluid insults, the gasketing characteristics were reduced.

Example 14 (Comparative)

ATTENDS Ultra Care normal absorbency pads were purchased in Europe in 1996. The product did not exhibit a complete gasketing contact with the wearer's body in the dry or wet product.

Example 15 (Comparative)

SERENITY STAYFREE Extra Plus pads manufactured by Johnson & Johnson were purchased in or near Neenah, Wis. in 1997. The dry product exhibited only minimal gasketing characteristics. The absorbent material bunches up during wear, defining crests and valleys of absorbent material. As the absorbent material is insulted with fluid, the fluid insulting the crests simply ran over the elastic sides of the pad. In addition, the absorption of fluid caused the absorbent material to swell upwards, resulting in the elastic sides being pushed further away from the wearer's body.

Example 16 (Comparative)

SERENITY Super Plus Guards manufactured by Johnson & Johnson were purchased in or near Neenah, Wis. in 1997. The dry product exhibited good gasketing characteristics. However, when insulted with fluid, the absorbent material swelled, pushing the thermal formed foam sides away from the wearer's body, breaking the gasketing contact.

Example 17

An absorbent pad of the type illustrated in FIGS. 1–5 was constructed and is designated as Example 17 in TABLE 2. The absorbent pad comprised a backsheet layer formed of a 0.028 mm. thick polyethylene film. An absorbent assembly of the type illustrated in FIG. 6 was disposed on the backsheet layer, and a topsheet layer was disposed on the absorbent assembly. The topsheet layer comprised a surfactant treated spunbond web of side-by-side bicomponent filaments with 50 percent polyethylene and 50 percent polypropylene having a basis weight of about 20 gsm.

The absorbent assembly comprised a fluid storage layer and an acquisition/distribution layer. The storage layer was formed of an air-laid mixture of 470 gsm wood pulp fibers and 305 gsm high-absorbency materials that was sandwiched between a pair of 19 gsm cellulose tissues. The storage layer was embossed using a matched male/male embossing roll. The acquisition/distribution layer comprised a through-air bonded carded web composed of a blend of 40 percent 6 denier polyester fibers and 60 percent 3 denier polypropylene/polyethylene side-by-side bicomponent fibers, with an overall basis weight of about 120 gsm. The storage layer was hourglass shaped and the acquisition/distribution layer was rectangular.

The absorbent pad included side flaps that extended along the full length of the side edges of the pad. The longitudinal ends of the side flaps were folded and bonded to themselves. As shown in FIGS. 1–5, the side flaps were formed by lateral portions of both the backsheet layer and the topsheet layer, and by portions of two separate side panel members. The side panel members comprised a high loft, fuzzy nonwoven spunbond made of side-by-side bicomponent filaments of 50 percent polyethylene and 50 percent polypropylene. The side panel members included folded regions that enclosed two 720 denier elastomeric threads. The threads were stretched 160 percent of their original length and operatively joined to the side panel members with a hot melt adhesive over a distance of 16.5 cm.

The Gurley stiffness values of ten absorbent pads were measured. The pads had an average Gurley stiffness of 1438 mg. at one end, with a standard deviation of 222 mg., and 1336 mg. at the other end, with a standard deviation of 269 mg.

Example 18

Another absorbent pad designated as Example 18 in TABLE 2 was constructed. The absorbent pad was similar to that of Example 17 except that the storage layer was embossed more aggressively.

The Gurley stiffness values of ten absorbent pads of Example 18 were measured. The pads had an average Gurley stiffness of 4,525 mg. at one end, with a standard deviation of 1372 mg., and 3,253 mg. at the other end, with a standard deviation of 1145 mg.

For purposes of comparison, absorbent pads designated Examples 19–26 were purchased and their Gibbosity Factor was measured.

Example 19 (Comparative)

POISE Extra Plus Absorbency pads manufactured by Kimberly-Clark Corporation were purchased in or near Appleton, Wis. on Oct. 15, 1996.

Example 20 (Comparative)

CERTINA Super pads were purchased in Europe in 1995. The Effective Elastic Value and the Elastic Out Of The Plane Value are based on measurements from 6 rather than 15 pads.

Example 21 (Comparative)

SERENITY STAYFREE Extra Plus pads manufactured by Johnson & Johnson were purchased in or near Appleton, Wis. on Oct. 15, 1996.

Example 22 (Comparative)

POISE Extra Absorbency pads manufactured by Kimberly-Clark Corporation were purchased in or near Appleton, Wis. in 1996.

Example 23 (Comparative)

POISE Regular Absorbency pads manufactured by Kimberly-Clark Corporation were purchased in or near Appleton, Wis. in 1996.

Example 24 (Comparative)

ATTENDS Regular absorbency pads manufactured by The Procter & Gamble Company were purchased in or near Appleton, Wis. in 1996.

Example 25 (Comparative)

ATTENDS Super absorbency pads manufactured by The Procter & Gamble Company were purchased in or near Appleton, Wis. in 1996.

Example 26 (Comparative)

OSCO Super As Long absorbency pads were purchased in or near Appleton, Wis. in 1996.

The Gibbosity factor was measured for each of the Examples 17–26. The results are presented in TABLE 2 below. For the pads of Examples 17–26, only the absorbent pads of the present invention (Examples 17 and 18) exhibited a gibbosity factor such that the elastic members of the absorbent pad interacted with the end of the absorbent pad and not simply causing bunching or wrinkling the absorbent assembly or core of the absorbent pad.

TABLE 2

| | Gibbosity Factor | | |
|---|---|---|---|
| Example | #Peaks/field (2 ¼") | Mean Ht. (mm) | Gibbosity (mm) |
| 17 | 11 | 0.82 | 9.02 |
| 18 | 0.8 | 0.66 | 0.528 |
| 19 | 76 | 1.51 | 114.76 |
| 20 | 35 | 1.64 | 57.4 |
| 21 | 22 | 1.03 | 22.66 |
| 22 | 55 | 1.07 | 58.85 |
| 23 | 70 | 1.03 | 72.1 |
| 24 | 24 | 0.79 | 18.96 |
| 25 | 38 | 1.05 | 39.9 |
| 26 | 55 | 0.98 | 53.9 |

It will be appreciated that the foregoing examples, given for purposes of illustration, are not to be construed as limiting the scope of this invention, which is defined by the following claims and all equivalents thereto.

We claim:

1. An absorbent pad defining a longitudinal axis, a transverse axis, opposite longitudinal end edges, and opposite longitudinal side edges extending between the longitudinal end edges, the absorbent pad comprising:

a backsheet layer;

a liquid permeable topsheet layer superposed on the backsheet layer;

an absorbent assembly sandwiched between the backsheet layer and the topsheet layer;

side flaps disposed transversely outward of the absorbent assembly, each side flap comprising an elastic member having opposite active ends that are longitudinally spaced from the respective longitudinal end edges of the absorbent pad; and garment attachment means disposed on the backsheet layer remote from the absorbent assembly, the garment attachment means positioned longitudinally outward of the active ends of the elastic members;

the absorbent pad having an Effective Elastic Value of at least 30 millimeters.

2. The absorbent pad of claim 1, wherein the absorbent pad has an Effective Elastic Value of at least about 40 millimeters.

3. The absorbent pad of claim 1, wherein the elastic members are completely out of the plane of the absorbent assembly when the absorbent pad is in a generally flat position.

4. The absorbent pad of claim 3, wherein the elastic members have an Elastic Out Of The Plane Value of at least about 5 millimeters.

5. The absorbent pad of claim 3, wherein the elastic members have an Elastic Out Of The Plane Value of from about 10 to about 30 millimeters.

6. The absorbent pad of claim 1, wherein the absorbent assembly has a thickness dimension of less than about 20 millimeters.

7. The absorbent pad of claim 6, wherein the absorbent assembly has a thickness dimension of less than about 10 millimeters.

8. The absorbent pad of claim 1, wherein the side flaps comprise a pair of nonwoven side panel members bonded to the backsheet and extending transversely outward of the absorbent assembly, the elastic members operatively joined to the side panel members.

9. The absorbent pad of claim 1, wherein the garment attachment means comprises an adhesive.

10. The absorbent pad of claim 1, wherein the absorbent pad has a length dimension of from about 10 to about 40 centimeters and a width dimension of from about 3 to about 12 centimeters.

11. An absorbent pad defining a longitudinal axis, a transverse axis, opposite longitudinal end edges, and opposite longitudinal side edges extending between the longitudinal end edges, the absorbent pad comprising:
  a backsheet layer;
  a fluid permeable topsheet layer superposed on the backsheet layer;
  a single layer absorbent core sandwiched between the backsheet layer and the topsheet layer;
  side flaps disposed transversely outward of the absorbent core, each side flap comprising an elastic member having opposite active ends that are longitudinally spaced from the respective longitudinal end edges of the absorbent pad; and
  garment attachment means disposed on the backsheet layer remote from the absorbent core, the garment attachment means positioned longitudinally outward of the active ends of the elastic members;
  the absorbent pad having an Effective Elastic Value of at least 30 millimeters.

12. The absorbent pad of claim 11, wherein the absorbent pad has an Effective Elastic Value of at least about 40 millimeters.

13. The absorbent pad of claim 11, wherein the elastic members are completely out of the plane of the absorbent core when the absorbent pad is in a generally flat position.

14. The absorbent pad of claim 13, wherein the elastic members have an Elastic Out Of The Plane Value of at least about 5 millimeters.

15. The absorbent pad of claim 13, wherein the elastic members have an Elastic Out Of The Plane Value of from about 10 to about 30 millimeters.

16. The absorbent pad of claim 11, wherein the absorbent core has a thickness dimension of less than about 20 millimeters.

17. The absorbent pad of claim 16 wherein the absorbent core has a thickness dimension of less than about 10 millimeters.

18. The absorbent pad of claim 11, wherein the side flaps comprise a pair of nonwoven side panel members bonded to the backsheet and extending transversely outward of the absorbent core, the elastic members operatively joined to the side panel members.

19. The absorbent pad of claim 11, wherein the garment attachment means comprises an adhesive.

20. The absorbent pad of claim 11, wherein the absorbent pad has a length dimension of from about 10 to about 40 centimeters and a width dimension of from about 3 to about 12 centimeters.

21. An absorbent pad defining a longitudinal axis, a transverse axis, opposite longitudinal end edges, and opposite longitudinal side edges extending between the longitudinal end edges, the absorbent pad comprising:
  a backsheet layer;
  a fluid permeable topsheet layer superposed on the backsheet layer;
  an absorbent assembly sandwiched between the backsheet layer and the topsheet layer;
  side flaps disposed transversely outward of the absorbent assembly comprising an proximal edge, a distal edge, a body-facing surface which is configured to be in a contacting relationship with a wearer's body during use, at least one elastic member having opposite active ends that are longitudinally spaced from the respective longitudinal end edges of the absorbent pad, wherein the proximal edge is attached to the longitudinal side edges of the absorbent pad and the distal edge remains unattached from the longitudinal side edges of the absorbent pad; and
  garment attachment means disposed on the backsheet layer remote from the absorbent assembly, the garment attachment means positioned longitudinally outward of the active ends of the elastic members;
  the absorbent pad having an Effective Elastic Value of at least 30 millimeters.

22. The absorbent pad of claim 21, wherein the side flaps are folded during use prior to an insult of fluid on the absorbent pad.

23. The absorbent pad of claim 21, wherein the side flaps are at least partially unfolded during use after at least one insult of fluid on the absorbent pad.

24. The absorbent pad of claim 21, wherein the side flaps are unfolded during use after at least one insult of fluid on the absorbent pad.

25. The absorbent pad of claim 22, 23, or 24, wherein the absorbent pad has an Effective Elastic Value of at least about 40 millimeters.

26. The absorbent pad of claim 22, 23, or 24, wherein the elastic members are completely out of the plane of the absorbent assembly when the absorbent pad is in a generally flat position.

27. The absorbent pad of claim 26, wherein the elastic members have an Elastic Out Of The Plane Value of at least about 5 millimeters.

28. The absorbent pad of claim 26, wherein the elastic members have an Elastic Out Of The Plane Value of from about 10 to about 30 millimeters.

29. The absorbent pad of claim 22, 23, or 24, wherein the absorbent assembly has a thickness dimension of less than about 20 millimeters.

30. The absorbent pad of claim 29, wherein the absorbent assembly has a thickness dimension of less than about 10 millimeters.

31. The absorbent pad of claim 22, 23, or 24, wherein the side flaps comprise a pair of nonwoven side panel members bonded to the backsheet and extending transversely outward of the absorbent assembly, the elastic members operatively joined to the side panel members.

32. The absorbent pad of claim 22, 23, or 24, wherein the garment attachment means comprises an adhesive.

33. The absorbent pad of claim 22, 23, or 24, wherein the absorbent pad has a length dimension of from about 10 to about 40 centimeters and a width dimension of from about 3 to about 3 centimeters.

34. An absorbent pad defining a longitudinal axis, a transverse axis, opposite longitudinal end edges, and opposite longitudinal side edges extending between the longitudinal end edges, the absorbent pad comprising:
 a backsheet layer;
 a fluid permeable topsheet layer superposed on the backsheet layer;
 an single layer absorbent core sandwiched between the backsheet layer and the topsheet layer;
 side flaps disposed transversely outward of the absorbent core comprising an proximal edge, a distal edge, a body-facing surface which is configured to be in a gasketing contact relationship with a wearer's body during use, at least one elastic member having opposite active ends that are longitudinally spaced from the respective longitudinal end edges of the absorbent pad, wherein the proximal edge is attached to the longitudinal side edges of the absorbent pad and the distal edge remains unattached from the longitudinal side edges of the absorbent pad; and
 garment attachment means disposed on the backsheet layer remote from the absorbent core, the garment attachment means positioned longitudinally outward of the active ends of the elastic members;
 the absorbent pad having an Effective Elastic Value of at least 30 millimeters.

35. The absorbent pad of claim 34, wherein the side flaps are folded during use prior to an insult of fluid on the absorbent pad.

36. The absorbent pad of claim 34, wherein the side flaps are at least partially unfolded during use after at least one insult of fluid on the absorbent pad.

37. The absorbent pad of claim 34, wherein the side flaps are unfolded during use after at least one insult of fluid on the absorbent pad.

38. The absorbent pad of claim 35, 36, or 37, wherein the absorbent pad has an Effective Elastic Value of at least about 40 millimeters.

39. The absorbent pad of claim 35, or 36, wherein the elastic members are completely out of the plane of the absorbent assembly when the absorbent pad is in a generally flat position.

40. The absorbent pad of claim 39, wherein the elastic members have an Elastic Out Of The Plane Value of at least about 5 millimeters.

41. The absorbent pad of claim 39, wherein the elastic members have an Elastic Out Of The Plane Value of from about 10 to about 30 millimeters.

42. The absorbent pad of claim 35, 36, or 37, wherein the absorbent assembly has a thickness dimension of less than about 20 millimeters.

43. The absorbent pad of claim 42, wherein the absorbent assembly has a thickness dimension of less than about 10 millimeters.

44. The absorbent pad of claim 35, 36, or 37, wherein the side flaps comprise a pair of nonwoven side panel members bonded to the backsheet and extending transversely outward of the absorbent assembly, the elastic members operatively joined to the side panel members.

45. The absorbent pad of claim 35, 36, or 37, wherein the garment attachment means comprises an adhesive.

46. The absorbent pad of claim 35, 36, or 37, wherein the absorbent pad has a length dimension of from about 10 to about 40 centimeters and a width dimension of from about 3 to about 12 centimeters.

47. An absorbent pad defining longitudinal and transverse axes, the absorbent pad comprising:
 a backsheet layer;
 a liquid permeable topsheet layer superposed on the backsheet layer;
 an absorbent assembly sandwiched between the backsheet layer and the topsheet layer; and
 side flaps disposed transversely outward of the absorbent assembly, each side flap comprising an elastic member that is at least partly out of the plane of the absorbent assembly when the absorbent pad is in a generally flat position;
 the absorbent pad having a Gibbosity Factor of less than about 18.

48. The absorbent pad of claim 47, wherein the absorbent pad has a Gurley stiffness of greater than about 2000 milligrams.

49. The absorbent pad of claim 47 or 48, wherein the absorbent pad has an Effective Elastic Value of at least 30 millimeters.

50. An absorbent pad defining a longitudinal axis, a transverse axis, opposite longitudinal end edges, and opposite longitudinal side edges extending between the longitudinal end edges, the absorbent pad comprising:
 a backsheet layer;
 a liquid permeable topsheet layer superposed on the backsheet layer;
 an absorbent assembly sandwiched between the backsheet layer and the topsheet layer;
 side flaps disposed transversely outward of the absorbent assembly, each side flap comprising an elastic member having opposite active ends that are longitudinally spaced from the respective longitudinal end edges of the absorbent pad; and
 garment attachment means disposed on the backsheet layer remote from the absorbent assembly, the garment attachment means positioned longitudinally outward of the active ends of the elastic members;
 the absorbent pad having a Gibbosity Factor of less than about 18.

51. The absorbent pad of claim 47, wherein:
 the elastic members have opposite active ends that are longitudinally spaced from respective longitudinal end edges of the absorbent pad; and
 garment attachment adhesive is disposed on the backsheet layer remote from the absorbent assembly, the garment attachment adhesive being positioned longitudinally outward of the active ends of the elastic members.

52. The absorbent pad of claim 50, wherein the absorbent pad has an Effective Elastic Value of at least 30 millimeters.

53. The absorbent pad of claim 50, wherein the absorbent pad has a Gurley Stiffness of greater than about 2000 milligrams.

54. The absorbent pad of claim 47, 50, or 51, wherein the absorbent pad has an Effective Elastic Value of at least about 40 millimeters.

55. The absorbent pad of claim 47 or 50, wherein the elastic members are completely out of the plane of the absorbent assembly when the absorbent pad is in a generally flat position.

56. The absorbent pad of claim 55, wherein the elastic members have an Elastic Out Of The Plane Value of at least about 5 millimeters.

57. The absorbent pad of claim 55, wherein the elastic members have an Elastic Out Of The Plane Value of from about 10 to about 100 millimeters.

58. The absorbent pad of claim 47 or 56, wherein the absorbent assembly has a thickness dimension of less than about 20 millimeters.

59. The absorbent pad of claim 58, wherein the absorbent assembly has a thickness dimension of less than about 10 millimeters.

60. The absorbent pad of claim 47 or 50, wherein the side flaps comprise a pair of nonwoven side panel members bonded to the backsheet and extending transversely outward of the absorbent assembly, the elastic members operatively joined to the side panel members.

61. The absorbent pad of claim 47 or 50, wherein the garment attachment means comprises an adhesive.

62. The absorbent pad of claim 47, 50 or 51, wherein the absorbent pad has a length dimension of from about 10 to about 40 centimeters and a width dimension of from about 3 to about 12 centimeters.

63. An absorbent pad defining longitudinal and transverse axes, the absorbent pad comprising:
- a backsheet layer;
- a fluid permeable topsheet layer superposed on the backsheet layer;
- a single layer absorbent core sandwiched between the backsheet layer and the topsheet layer; and
- side flaps disposed transversely outward of the absorbent assembly, each side flap comprising an elastic member that is at least partly out of the plane of the absorbent core when the absorbent pad is in a generally flat position;
- the absorbent pad having a Gibbosity Factor of less than about 18.

64. An absorbent pad defining a longitudinal axis, a transverse axis, opposite longitudinal end edges, and opposite longitudinal side edges extending between the longitudinal end edges, the absorbent pad comprising:
- a backsheet layer;
- a fluid permeable topsheet layer superposed on the backsheet layer;
- a single layer absorbent core sandwiched between the backsheet layer and the topsheet layer;
- side flaps disposed transversely outward of the absorbent core, each side flap comprising an elastic member having opposite active ends that are longitudinally spaced from the respective longitudinal end edges of the absorbent pad; and
- garment attachment means disposed on the backsheet layer remote from the absorbent core, the garment attachment means positioned longitudinally outward of the active ends of the elastic members;
- the absorbent pad having a Gibbosity Factor of less than about 18.

65. The absorbent pad of claim 63, wherein:
- the elastic members have opposite active ends that are longitudinally spaced from respective longitudinal end edges of the absorbent pad; and
- garment attachment adhesive is disposed on the backsheet layer remote from the absorbent core, the garment attachment adhesive being positioned longitudinally outward of the active ends of the elastic members.

66. The absorbent pad of claim 63, 64, or 65, wherein the absorbent pad has an Effective Elastic Value of at least 30 millimeters.

67. The absorbent pad of claim 63, 64, or 65, wherein the absorbent pad has an Effective Elastic Value of at least about 40 millimeters.

68. The absorbent pad of claim 63, 64, or 65, wherein the absorbent pad has a Gurley Stiffness of greater than about 800 milligrams.

69. The absorbent pad of claim 63 or 64, wherein the elastic members are completely out of the plane of the absorbent core when the absorbent pad is in a generally flat position.

70. The absorbent pad of claim 69, wherein the elastic members have an Elastic Out Of The Plane Value of at least about 5 millimeters.

71. The absorbent pad of claim 69, wherein the elastic members have an Elastic Out Of The Plane Value of from about 10 to about 30 millimeters.

72. The absorbent pad of claim 63 or 64, wherein the absorbent core has a thickness dimension of less than about 20 millimeters.

73. The absorbent pad of claim 72, wherein the absorbent core has a thickness dimension of less than about 10 millimeters.

74. The absorbent pad of claim 63 or 64, wherein the side flaps comprise a pair of nonwoven side panel members bonded to the backsheet and extending transversely outward of the absorbent core, the elastic members operatively joined to the side panel members.

75. The absorbent pad of claim 63, or 64, wherein the garment attachment means comprises an adhesive.

76. The absorbent pad of claim 63, 64 or 65, wherein the absorbent pad has a length dimension of from about 10 to about 40 centimeters and a width dimension of from about 3 to about 12 centimeters.

77. An absorbent pad defining longitudinal and transverse axes, the absorbent pad comprising:
- a backsheet layer;
- a fluid permeable topsheet layer superposed on the backsheet layer;
- an absorbent assembly sandwiched between the backsheet layer and the topsheet layer; and,
- side flaps disposed transversely outward of the absorbent assembly, each side flap comprising an elastic member that is at least partly out of the plane of the absorbent assembly when the absorbent pad is in a generally flat position and wherein each side flap maintains a gasketing contact relationship with a wearer's body during use,
wherein the absorbent pad has a Gibbosity Factor of less than about 18.

78. The absorbent pad of claim 77, wherein the absorbent pad has a Gurley stiffness of greater than about 2000 milligrams.

79. The absorbent pad of claim 77, wherein the side flaps are folded during use prior to an insult of fluid on the absorbent pad.

80. The absorbent pad of claim 77, wherein the side flaps are at least partially unfolded during use after at least one insult of fluid on the absorbent pad.

81. The absorbent pad of claim 77, wherein the side flaps are unfolded during use after at least one insult of fluid on the absorbent pad.

82. An absorbent pad defining a longitudinal axis, a transverse axis, opposite longitudinal end edges, and opposite longitudinal side edges extending between the longitudinal end edges, the absorbent pad comprising:

a backsheet layer;

a fluid permeable topsheet layer superposed on the backsheet layer;

an absorbent assembly sandwiched between the backsheet layer and the topsheet layer;

side flaps disposed transversely outward of the absorbent assembly comprising an proximal edge, a distal edge, a body-facing surface which is configured to be in a contacting relationship with a wearer's body during use, at least one elastic member having opposite active ends that are longitudinally spaced from the respective longitudinal end edges of the absorbent pad, wherein the proximal edge is attached to the longitudinal side edges of the absorbent pad and the distal edge remains unattached from the longitudinal side edges the absorbent pad; and garment attachment means disposed on the backsheet layer remote from the absorbent assembly, the garment means positioned longitudinally outward of the active ends of the elastic members;

the absorbent pad having a Gibbosity Factor of less than about 18.

83. The absorbent pad f claim 82, wherein the absorbent pad has an Effective Elastic Value of at least 30 millimeters.

84. The absorbent pad of claim 82, wherein the side flaps are folded during use prior to an insult of fluid on the absorbent pad.

85. The absorbent pad of claim 82, wherein the side flaps are at least partially unfolded during use after at least one insult of fluid on the absorbent pad.

86. The absorbent pad of claim 82, wherein the side flaps are unfolded during use after at least one insult of fluid on the absorbent pad.

87. The absorbent pad of claim 77, wherein:

the elastic members have opposite active ends that are longitudinally spaced from respective longitudinal end edges of the absorbent pad; and garment attachment adhesive is disposed on the backsheet layer remote from the absorbent assembly, the garment attachment adhesive being positioned longitudinally outward of the active ends of the elastic members.

88. The absorbent pad of claim 79, 80, 81, 82 or 87, wherein the absorbent pad has an Effective Elastic Value of at least 30 millimeters.

89. The absorbent pad of claim 79, 80, 81, 82, 84, 85, or 86, wherein the absorbent pad has an Effective Elastic Value of at least about 40 millimeters.

90. The absorbent pad of claim 79 80, 81, 82, 84, 85, or 86, wherein the elastic members are completely out of the plane of the absorbent assembly when the absorbent pad is in a general flat position.

91. The absorbent pad of claim 90, wherein the elastic members have an Elastic Out Of The Plane Value of at least about 5 millimeters.

92. The absorbent pad of claim 90, wherein the elastic members have an Elastic Out Of The Plane Value from about 10 to about 30 millimeters.

93. The absorbent pad of claim 79, 80, 81, 84, 85 or 86, wherein the absorbent assembly has a thickness dimension of less than about 20 millimeters.

94. The absorbent pad of claim 93, wherein the absorbent assembly has a thickness dimension of less than about 10 millimeters.

95. The absorbent pad of claim 79, 80, 81, 84, 85, or 86, wherein the side flaps comprise a pair of nonwoven side panel members bonded to the backsheet and extending transversely outward of the absorbent assembly, the elastic members operatively joined to the side panel members.

96. The absorbent pad of claim 79, 80, 81, 84, 85, or 86, wherein the garment attachment means comprises an adhesive.

97. The absorbent pad of claim 79, 80, 81, 84, 85, 86 or 87, wherein the absorbent pad has a length dimension of from about 10 to about 40 centimeters and a width dimension of from about 3 to about 12 centimeters.

98. An absorbent pad defining longitudinal and transverse axes, the absorbent pad comprising:

a backsheet layer;

a fluid permeable topsheet layer superposed on the backsheet layer;

a single layer absorbent core sandwiched between the backsheet layer and the topsheet layer; and, side flaps disposed transversely outward of the absorbent core, each side flap comprising an elastic member that is at least partly out of the plane of the absorbent core when the absorbent pad is in a generally flat position and wherein each side flap maintains a gasketing contact relationship with a wearer's body during use, wherein the absorbent pad has a Gibbosity Factor of less than about 18.

99. The absorbent pad of claim 98, wherein the absorbent pad has a Gurley stiffness of at least about 800 milligrams.

100. The absorbent pad of claim 98, wherein the side flaps are folded during use prior to an insult of fluid on the absorbent pad.

101. The absorbent pad of claim 98, wherein the side flaps are at least partially unfolded during use after at least one insult of fluid on the absorbent pad.

102. The absorbent pad of claim 98, wherein the side flaps are unfolded during use after at least one insult of fluid on the absorbent pad.

103. An absorbent pad defining a longitudinal axis, a transverse axis, opposite longitudinal end edges, and opposite longitudinal side edges extending between the longitudinal end edges, the absorbent pad comprising:

a backsheet layer;

a fluid permeable topsheet layer superposed on the backsheet layer;

an single layer absorbent core sandwiched between the backsheet layer and the topsheet layer;

side flaps disposed transversely outward of the absorbent core comprising an proximal edge, a distal edge, a body-facing surface which is configured to be in a gasketing contact relationship with a wearer's body during use, at least one elastic member having opposite active ends that are longitudinally spaced from the respective longitudinal end edges of the absorbent pad, wherein the proximal edge is attached to the longitudinal side edges of the absorbent pad and the distal edge remains unattached from the longitudinal side edges of the absorbent pad; and garment attachment means disposed on the backsheet layer remote from the absorbent core, the garment attachment means positioned longitudinally outward of the active ends of the elastic members, wherein the absorbent pad has a Gibbosity Factor of less than about 18.

104. The absorbent pad of claim 103, wherein the absorbent pad has an Effective Elastic Value of at least 30 millimeters.

105. The absorbent pad of claim 103, wherein the side flaps are folded during use prior to an insult of fluid on the absorbent pad.

106. The absorbent pad of claim 103, wherein the side flaps are at least partially unfolded during use after at least one insult of fluid on the absorbent pad.

107. The absorbent pad of claim 103, wherein the side flaps are unfolded during use after at least one insult of fluid on the absorbent pad.

108. The absorbent pad of claim 98, wherein:
the elastic members have opposite active ends that are longitudinally spaced from respective longitudinal end edges of the absorbent pad; and
garment attachment adhesive is disposed on the backsheet layer remote from the absorbent assembly, the garment attachment adhesive being positioned longitudinally outward of the active ends of the elastic members.

109. The absorbent pad of claim 98, 100, 101, 102, or 108, wherein the absorbent pad has an Effective Elastic Value of at least 30 millimeters.

110. The absorbent pad of claim 98, 100, 101, 102, 105 106, or 107, wherein the absorbent pad has an Effective Elastic Value of at least about 40 millimeters.

111. The absorbent pad of claim 98, 100, 101, 102, 105, 106, or 108, wherein the elastic members are completely out of the plane of the absorbent assembly when the absorbent pad is in a generally flat position.

112. The absorbent pad of claim 103, wherein the elastic members have an Elastic Out Of The Plane Value of at least about 5 millimeters.

113. The absorbent pad of claim 111, wherein the elastic members have an Elastic Out Of The Plane Value of from about 10 to about 30 millimeters.

114. The absorbent pad of claim 100, 101, 102, 105, 106, or 107, wherein the absorbent assembly has a thickness dimension of less than about 20 millimeters.

115. The absorbent pad of claim 114, wherein the absorbent assembly has a thickness dimension of less than about 10 millimeters.

116. The absorbent pad of claim 100, 101, 102, 105, 106, or 107, wherein the side flaps comprise a pair of nonwoven side panel members bonded to the backsheet and extending transversely outward of the absorbent assembly, the elastic members operatively joined to the side panel members.

117. The absorbent pad of claim 100, 101, 102, 105, 106, or 107, wherein the garment attachment means comprises an adhesive.

118. The absorbent pad of claim 100, 101, 102, 105, 106, 107, or 108, wherein the absorbent pad has a length dimension of from about 10 to about 40 centimeters and a width dimension of from about 3 to about 12 centimeters.

* * * * *

UNITED STATES PATENT AND TRADEMARK OFFICE
CERTIFICATE OF CORRECTION

PATENT NO.    : 6,315,765 B1
DATED         : November 13, 2001
INVENTOR(S)   : Paul Joseph Datta, Kathy Geralyn Richardson, Sirlei Auler Waterhouse and Bernhardt Edward It is certified that error appears in the above-identified patent and that said Letters Patent is hereby corrected as shown below:

Column 33,
Line 8, delete "3" after "about" and substitute -- 12 --.

Signed and Sealed this

Eighth Day of October, 2002

Attest:

JAMES E. ROGAN
Attesting Officer    Director of the United States Patent and Trademark Office